(12) United States Patent
Mazar

(10) Patent No.: US 7,065,409 B2
(45) Date of Patent: Jun. 20, 2006

(54) DEVICE COMMUNICATIONS OF AN IMPLANTABLE MEDICAL DEVICE AND AN EXTERNAL SYSTEM

(75) Inventor: Scott T. Mazar, Inver Grove Heights, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 475 days.

(21) Appl. No.: 10/318,469

(22) Filed: Dec. 13, 2002

(65) Prior Publication Data

US 2004/0116981 A1    Jun. 17, 2004

(51) Int. Cl.
*A61N 1/18* (2006.01)

(52) U.S. Cl. .......................... 607/60; 607/128; 607/32; 607/31; 128/903

(58) Field of Classification Search ................ 607/128, 607/60, 32, 31; 128/903
See application file for complete search history.

(56) References Cited

U.S. PATENT DOCUMENTS

| | | | |
|---|---|---|---|
| 4,361,153 A * | 11/1982 | Slocum et al. ................ | 607/32 |
| 4,561,443 A | 12/1985 | Hogrefe et al. ............. | 128/419 |
| 4,658,831 A | 4/1987 | Reinhard et al. ........... | 128/697 |
| 4,681,111 A | 7/1987 | Silvian ........................ | 128/419 |
| 4,705,043 A | 11/1987 | Imran .......................... | 128/419 |
| 4,757,816 A | 7/1988 | Ryan et al. .................. | 128/419 |
| 4,793,353 A | 12/1988 | Borkan ........................ | 128/421 |
| 4,809,697 A | 3/1989 | Causey, III et al. ........ | 128/419 |
| 4,932,408 A | 6/1990 | Schaldach ................... | 128/419 |
| 4,947,407 A | 8/1990 | Silvian ........................ | 375/94 |
| 4,969,464 A | 11/1990 | Callaghan et al. .......... | 128/419 |
| 5,058,581 A | 10/1991 | Silvian ........................ | 128/419 |
| 5,081,987 A | 1/1992 | Nigam ........................ | 120/419 |
| 5,113,869 A | 5/1992 | Nappholz et al. ........... | 128/696 |
| 5,117,825 A | 6/1992 | Grevious ..................... | 128/419 |
| 5,137,022 A | 8/1992 | Henry .......................... | 128/419 |
| 5,241,961 A | 9/1993 | Henry .......................... | 607/32 |
| 5,292,343 A | 3/1994 | Blanchette et al. .......... | 607/32 |
| 5,331,966 A | 7/1994 | Bennett et al. .............. | 128/696 |
| 5,342,408 A * | 8/1994 | deCoriolis et al. ........... | 607/32 |
| 5,350,411 A | 9/1994 | Ryan et al. ................... | 607/32 |
| 5,383,915 A * | 1/1995 | Adams ........................ | 607/60 |
| 5,413,594 A | 5/1995 | Williams ..................... | 607/32 |
| 5,415,181 A | 5/1995 | Hogrefe et al. ............. | 128/736 |
| 5,458,122 A | 10/1995 | Hethuin ....................... | 128/696 |

(Continued)

FOREIGN PATENT DOCUMENTS

EP          0 554 955 A1    8/1993

*Primary Examiner*—Robert E. Pezzuto
*Assistant Examiner*—Deborah Malamud
(74) *Attorney, Agent, or Firm*—Schwegman, Lundberg, Woessner & Kluth, P.A.

(57) ABSTRACT

An implantable medical device, external unit, and method for establishing communication between them are disclosed. The external unit learns the frequencies of transmission and reception for the implant. The transmit frequency of the implant is learned by the external unit measuring a difference between the transmit frequency of the implant and the external unit's receive frequency. The receive frequency of the implant is learned by the measured difference between its transmit frequency and the receive frequency of the external unit when the implant has a fixed transmit and receive frequency difference. Otherwise, the receive frequency is learned by the implant measuring the difference between its receive frequency and the transmit frequency of the external unit and by sending an indication of the difference to the external unit through the return signal. The external unit may anticipate a beginning of the implant's preset communication period based on its internal clock.

43 Claims, 11 Drawing Sheets

U.S. PATENT DOCUMENTS

| | | | |
|---|---|---|---|
| 5,466,246 A * | 11/1995 | Silvian | 607/32 |
| 5,476,485 A | 12/1995 | Weinberg et al. | 607/28 |
| 5,481,262 A | 1/1996 | Urbas et al. | 340/870.17 |
| 5,509,927 A | 4/1996 | Epstein et al. | 607/32 |
| 5,522,865 A | 6/1996 | Schulman et al. | 607/56 |
| 5,549,654 A | 8/1996 | Powell | 607/32 |
| 5,626,625 A * | 5/1997 | Fernald | 607/32 |
| 5,626,630 A | 5/1997 | Markowitz et al. | 607/60 |
| 5,629,678 A | 5/1997 | Gargano et al. | 340/573 |
| 5,630,836 A | 5/1997 | Prem et al. | 607/61 |
| 5,674,249 A | 10/1997 | De Coriolis et al. | 607/5 |
| 5,683,432 A | 11/1997 | Goedeke et al. | 607/32 |
| 5,713,937 A | 2/1998 | Nappholz et al. | 607/30 |
| 5,741,315 A | 4/1998 | Lee et al. | 607/60 |
| 5,743,267 A | 4/1998 | Nikolic et al. | 128/673 |
| 5,752,976 A | 5/1998 | Duffin et al. | 607/32 |
| 5,752,977 A | 5/1998 | Grevious et al. | 607/32 |
| 5,766,232 A | 6/1998 | Grevious et al. | 607/60 |
| 5,769,876 A | 6/1998 | Silvian | 607/60 |
| 5,772,586 A | 6/1998 | Heinonen et al. | 600/300 |
| 5,774,501 A | 6/1998 | Halpern et al. | 375/279 |
| 5,782,890 A * | 7/1998 | Wahlstrand et al. | 607/32 |
| 5,791,342 A | 8/1998 | Woodard | 128/630 |
| 5,792,207 A | 8/1998 | Dietrich | 607/32 |
| 5,814,089 A | 9/1998 | Stokes et al. | 607/32 |
| 5,836,983 A | 11/1998 | Weijand et al. | 607/9 |
| 5,843,133 A | 12/1998 | Routh et al. | 607/14 |
| 5,843,139 A | 12/1998 | Goedeke et al. | 607/32 |
| 5,861,014 A | 1/1999 | Familoni | 607/40 |
| 5,861,018 A | 1/1999 | Feierbach | 607/60 |
| 5,899,928 A | 5/1999 | Sholder et al. | 607/27 |
| 5,899,931 A * | 5/1999 | Deschamp et al. | 607/60 |
| 5,917,414 A | 6/1999 | Oppelt et al. | 340/573.1 |
| 5,919,214 A | 7/1999 | Ciciarelli et al. | 607/32 |
| 5,935,078 A | 8/1999 | Feierbach | 600/509 |
| 5,944,659 A | 8/1999 | Flach et al. | 600/300 |
| 5,957,861 A | 9/1999 | Combs et al. | 600/547 |
| 5,963,650 A * | 10/1999 | Simionescu et al. | 705/63 |
| 5,999,857 A | 12/1999 | Weijand et al. | 607/60 |
| 6,083,248 A | 7/2000 | Thompson | 607/30 |
| 6,093,146 A | 7/2000 | Filangeri | 600/300 |
| 6,106,551 A * | 8/2000 | Crossett et al. | 623/3.28 |
| 6,115,636 A | 9/2000 | Ryan | 607/60 |
| 6,141,584 A | 10/2000 | Rockwell et al. | 607/5 |
| 6,150,951 A * | 11/2000 | Olejniczak | 340/2.8 |
| 6,170,488 B1 | 1/2001 | Spillman, Jr. et al. | 128/899 |
| 6,185,452 B1 | 2/2001 | Schulman et al. | 604/20 |
| 6,200,264 B1 | 3/2001 | Satherley et al. | 600/300 |
| 6,201,993 B1 | 3/2001 | Kruse et al. | 607/30 |
| 6,203,495 B1 | 3/2001 | Bardy | 600/301 |
| 6,206,835 B1 | 3/2001 | Spillman, Jr. et al. | 600/485 |
| 6,208,894 B1 | 3/2001 | Schulman et al. | 607/2 |
| 6,213,942 B1 | 4/2001 | Flach et al. | 600/300 |
| 6,216,038 B1 | 4/2001 | Hartlaub et al. | 607/31 |
| 6,221,011 B1 | 4/2001 | Bardy | 600/300 |
| 6,223,083 B1 | 4/2001 | Rosar | 607/60 |
| 6,236,889 B1 | 5/2001 | Soykan et al. | 607/30 |
| 6,240,317 B1 | 5/2001 | Villaseca et al. | 607/60 |
| 6,250,309 B1 * | 6/2001 | Krichen et al. | 128/899 |
| 6,261,230 B1 | 7/2001 | Bardy | 600/300 |
| 6,263,245 B1 | 7/2001 | Snell | 607/60 |
| 6,263,246 B1 | 7/2001 | Goedeke et al. | 607/60 |
| 6,263,247 B1 | 7/2001 | Mueller et al. | 607/60 |
| 6,289,238 B1 | 9/2001 | Besson et al. | 600/509 |
| 6,292,698 B1 | 9/2001 | Duffin et al. | 607/32 |
| 6,295,466 B1 | 9/2001 | Ishikawa et al. | 600/509 |
| 6,298,271 B1 | 10/2001 | Weijand | 607/60 |
| 6,304,788 B1 | 10/2001 | Eady et al. | 700/86 |
| 6,319,200 B1 | 11/2001 | Lai et al. | 600/300 |
| 6,329,929 B1 | 12/2001 | Weijand et al. | 340/870.25 |
| 6,345,203 B1 | 2/2002 | Mueller et al. | 607/60 |
| 6,349,234 B1 | 2/2002 | Pauly et al. | 607/60 |
| 6,363,282 B1 | 3/2002 | Nichols et al. | 607/30 |
| 6,379,300 B1 * | 4/2002 | Haubrich | 600/300 |
| 6,418,346 B1 | 7/2002 | Nelson et al. | 607/59 |
| 6,434,429 B1 * | 8/2002 | Kraus et al. | 607/60 |
| 6,442,432 B1 | 8/2002 | Lee | 607/59 |
| 6,442,433 B1 | 8/2002 | Linberg | 607/60 |
| 6,477,242 B1 | 11/2002 | Freeny, Jr. | 379/93.24 |
| 6,480,744 B1 * | 11/2002 | Ferek-Petric | 607/60 |
| 6,480,745 B1 | 11/2002 | Nelson et al. | 607/60 |
| 6,482,156 B1 * | 11/2002 | Iliff | 600/300 |
| 6,602,191 B1 * | 8/2003 | Quy | 600/300 |
| 6,763,269 B1 * | 7/2004 | Cox | 607/60 |
| 6,878,111 B1 * | 4/2005 | Kenknight et al. | 600/300 |
| 2001/0012955 A1 | 8/2001 | Goedeke et al. | 607/27 |
| 2001/0023360 A1 | 9/2001 | Nelson et al. | 607/60 |
| 2001/0025137 A1 | 9/2001 | Webb et al. | 600/300 |
| 2001/0025189 A1 | 9/2001 | Haueter et al. | 607/62 |
| 2001/0027331 A1 | 10/2001 | Thompson | 607/60 |
| 2001/0027349 A1 | 10/2001 | Eady et al. | 700/17 |
| 2001/0029321 A1 | 10/2001 | Beetz et al. | 600/300 |
| 2001/0031998 A1 | 10/2001 | Nelson et al. | 607/60 |
| 2001/0037056 A1 | 11/2001 | Nunome | 600/300 |
| 2001/0039372 A1 | 11/2001 | Yasushi et al. | 600/300 |
| 2001/0044588 A1 | 11/2001 | Mault | 600/549 |
| 2001/0047125 A1 | 11/2001 | Quy | 600/300 |
| 2001/0051764 A1 | 12/2001 | Bardy | 600/300 |
| 2001/0051787 A1 | 12/2001 | Haller et al. | 604/66 |
| 2002/0013517 A1 | 1/2002 | West et al. | 600/300 |
| 2002/0013518 A1 | 1/2002 | West et al. | 600/300 |
| 2002/0013538 A1 | 1/2002 | Teller | 600/549 |
| 2002/0013613 A1 | 1/2002 | Haller et al. | 607/60 |
| 2002/0013614 A1 | 1/2002 | Thompson | 607/60 |
| 2002/0019584 A1 | 2/2002 | Schulze et al. | 600/300 |
| 2002/0019586 A1 | 2/2002 | Teller et al. | 600/300 |
| 2002/0028988 A1 | 3/2002 | Suzuki et al. | 600/300 |
| 2002/0033247 A1 | 3/2002 | Linberg | 607/60 |
| 2002/0040234 A1 | 4/2002 | Linberg | 607/32 |
| 2002/0052539 A1 | 5/2002 | Haller et al. | 600/300 |
| 2002/0072785 A1 | 6/2002 | Nelson et al. | 607/60 |
| 2002/0082665 A1 | 6/2002 | Haller et al. | 607/60 |
| 2002/0095196 A1 | 7/2002 | Linberg | 607/60 |
| 2002/0111542 A1 | 8/2002 | Warkentin et al. | 600/300 |

* cited by examiner

DEVICE COMMUNICATIONS OF AN IMPLANTABLE MEDICAL DEVICE AND AN EXTERNAL SYSTEM

TECHNICAL FIELD

The present system relates generally to advanced patient management systems, and particularly, but not by way of limitation, to such a system whereby an implantable medical device of a patient communicates with an external device.

BACKGROUND OF THE INVENTION

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, COPD, chronic pain, and epilepsy, is event driven, where acute de-compensations result in hospitalization. In addition to causing considerable physical and emotional trauma to the patient and family, event driven hospitalizations consume a majority of the total health care expenditure allocated to the treatment of heart failure.

Hospitalization and treatment for an acute de-compensation typically occurs after the de-compensation event has happened. However, most heart failure patients exhibit prior non-traumatic symptoms, such as steady weight gain, in the weeks or days prior to the de compensation. If the caregiver is aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise. Such intervention is usually effective in preventing the de-compensation episode and thus avoiding hospitalization.

Patients with chronic heart disease can receive implantable cardiac devices such as pacemakers, implantable cardioverter defibrillators (ICDs), and heart failure cardiac resynchronization therapy (CRT) devices. Currently, the electrophysiologist that implants pacemakers and ICDs requires their patients to make clinic visits periodically, usually once every three or four months, in order to verify if their implanted device is working correctly and programmed optimally. Device follow-ups are usually performed by the nurse-staff assisted by the sales representative from the device manufacturers. Device follow-ups are labor intensive and typically require patients to make multiple clinic visits.

In an effort to limit the number of follow-ups necessary to monitor the device and the data that it acquires, an advanced patient management system may provide a communication infrastructure. This infrastructure allows the implantable medical device to communicate over long distances at virtually any time with a backend system that monitors the implantable device and the patient. Furthermore, this backend system allows monitoring of the patient on a more frequent basis than ordinary follow-up visits can practically allow. The back end system communicates with the implantable device through an external unit such as a repeater that the patient keeps in close proximity. Conventionally, the external unit communicates directly with the implantable device through inductive coupling which requires that the patient hold a wand over the location of the implant. The external unit then transfers information from the implantable device through a telephone line interface to the back end system.

The conventional approach to communicating with the implantable device has drawbacks in that the patient must actively participate in the communication process. The inductive coupling provides little range between the implant and the external unit, and therefore, the patient must be in close proximity during the communication process. However, radio frequency communications at higher frequencies than those used for inductive coupling are a viable option. Radio frequency communications provide much greater range between the external unit and the implant and allow the communication to occur automatically without patient intervention. However, providing automatic radio frequency communications abilities in the implant can lead to significant increases in cost, size, and power consumption.

The radio frequencies of transmission and reception by the implantable device are fairly unpredictable when using low-cost transceivers, such as surface acoustic wave (SAW) based devices, due to environmental effects and manufacturing tolerances. Therefore, the external unit cannot communicate with the implant at exactly the same frequencies each time. Furthermore, providing frequency synthesis in the implant to control the frequencies of transmission and reception is not a practical solution because frequency synthesis consumes more power than can be provided over a long-term basis, which is required by implants with lengthy life times. Therefore, radio frequency communications with the implant are troublesome.

Additionally, automatic and periodic radio frequency communications between the implant and external unit require that the implant and the external unit expect to communicate at the same time. The communication must be periodic to reduce the power consumption required by the communications devices within the implant. However, environmental effects and manufacturing tolerances cause time drift between the clock of the implant and the clock of the external unit. The uncertainty as to the proper time to communicate can cause the implant to power up in anticipation for communication at a different time than when the external unit attempts to communicate. Therefore, opportunities to communicate may be completely lost because the devices are not properly synchronized.

SUMMARY OF THE INVENTION

Embodiments of the present invention address these problems and others by providing communications processes between the repeater and the implantable medical device. The implant and the repeater may be configured so that the repeater learns and adapts to the appropriate frequencies for transmission and reception. Additionally, the implant and repeater may be configured to anticipate and compensate for a lack of synchronization between the internal clock of the implant and the internal clock of the repeater.

Communication may be established between an implantable medical device and an external unit wherein the implantable medical device has a transmit and a receive frequency that are separated by a fixed difference. One or more signals are sent out from a transmitter of the external unit, and one signal of the one or more signals has a frequency that is close enough to the receive frequency for the implantable device to receive the one signal. A receiver of the implantable device receives the one signal, and a transmitter of the implantable device sends out a return signal at a transmit frequency in response to receiving the one signal. The receiver of the external unit receives the return signal and a frequency discriminator of the receiver measures a difference between the transmit frequency of the return signal and a receive frequency of the external unit. A processor of the external unit then alters the transmit frequency and receive frequency of the external unit by the measured difference.

Alternatively, communication may be established between an implantable medical device and an external unit wherein the implantable medical device has a transmit frequency and a receive frequency. A transmitter of the external unit sends out one or more signals wherein one signal of the one or more signals has a frequency that is close enough to the receive frequency for the implantable device to receive the one signal. A receiver of the implantable device receives the one signal and measures a first difference between the frequency of the one signal and the receive frequency. The transmitter of the implantable device sends out a return signal at the transmit frequency from the implantable medical device in response to receiving the first signal, wherein the return signal includes an indication of the first difference. The receiver of the external unit receives the return signal and a processor of the external unit detects the first difference from the indication included in the return signal. A frequency discriminator of the external unit measures a second difference between the transmit frequency of the return signal and a receive frequency of the external unit, and the processor of the external unit alters the transmit frequency of the external unit by the first difference and alters the receive frequency of the external unit by the second difference.

Additionally, communication may be periodically established between an implantable medical device and an external unit wherein the implantable medical device has a clock that triggers a preset communication period. An initial communication is established between the external unit and the implantable medical device. A clock in the external unit is synchronized with the clock of the implantable medical device during the initial communication. After the initial communication is terminated, a time is detected with the clock of the external unit that is earlier than the preset communication period by a preset amount as measured by the clock of the external unit. A signal is sent on one or more frequencies from a transmitter of the external unit beginning at the detected time and extending for an amount of time greater than the preset communication period as measured by the clock of the external unit or until a return signal is received by the receiver of the external unit from the implantable device.

These and various other features as well as advantages, which characterize the present invention, will be apparent from a reading of the following detailed description and a review of the associated drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Prior to discussing the devices and communication protocols of the embodiments of the present invention, an example of an advanced patient management system is discussed to provide an example of an environmental context for the embodiments of the present invention. However, it is to be understood that the advanced patient management system described herein in conjunction with the embodiments of the present invention is only one example of an operating environment and it not to be taken in a limiting sense. For example, the embodiments of the present invention involving communication between an external device and an implantable medical device may operate without further interaction with an advanced patient management system and its associated communication system. The devices and communication protocols of the embodiments of the present invention are discussed below with reference to FIGS. 5–16 in section V. DEVICE COMMUNICATIONS.

An advanced patient management system is configured to collect patient-specific information, store and collate the information, and generate actionable recommendations to enable the predictive management of patients. The advanced patient management system is also configured to leverage a remote communications infrastructure to provide automatic device follow-ups to collect data, coordinate therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 1:
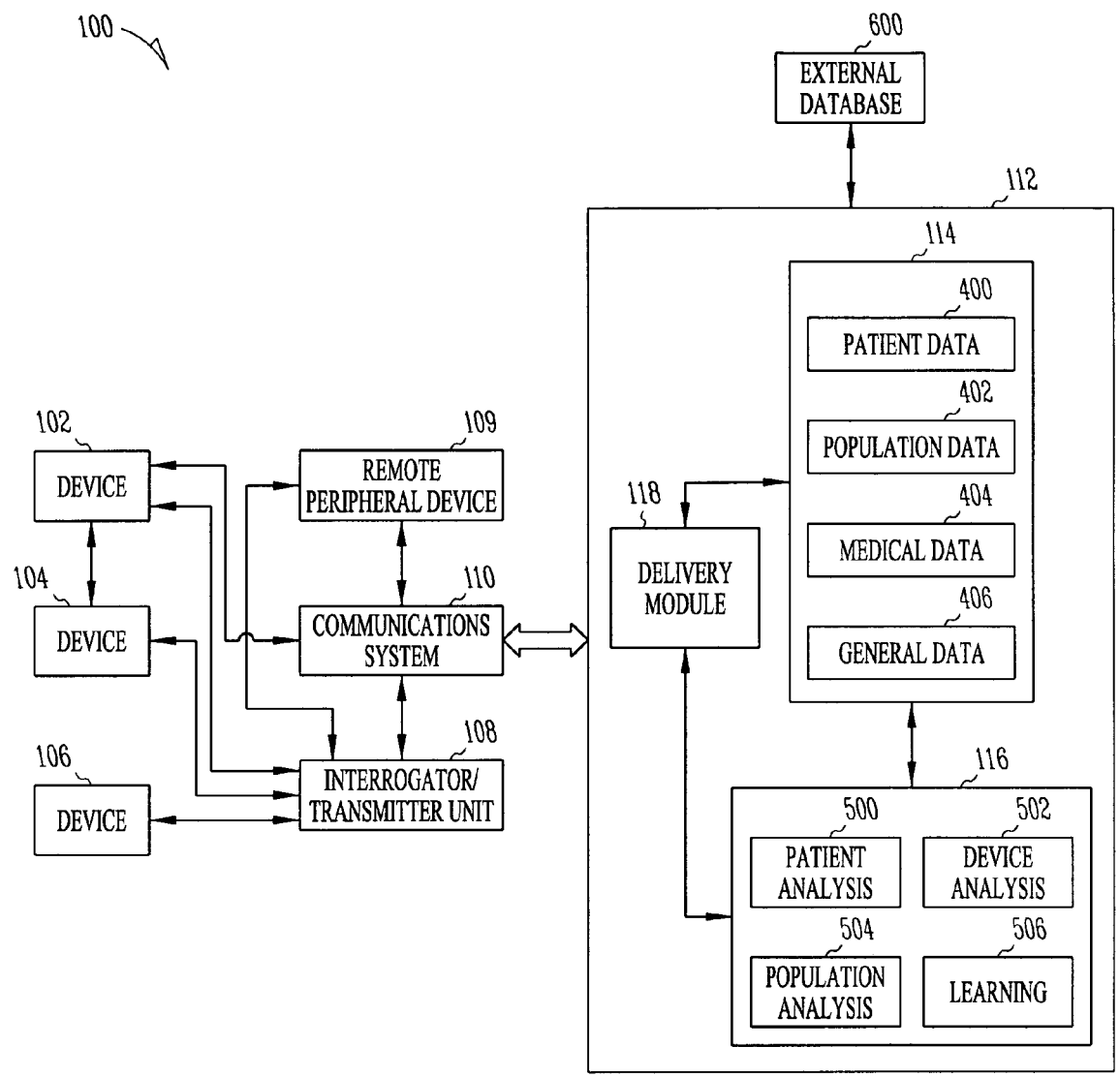
FIG. 1 illustrates an advanced patient management system.

FIG. 1 illustrates an example advanced patient management system 100. Advanced patient management system 100 generally includes the following components: one or more devices 102, 104, and 106, one or more interrogator/transceiver units 108, a communication system 110, one or more remote peripheral devices 109, and a host 112.

Each component of the advanced patient management system 100 can communicate using the communication system 110. Some components may also communicate directly with one another. For example, devices 102 and 104 may be configured to communicate directly with one another. The various components of the example advanced patient management system 100 illustrated herein are described below.

I. Devices

Devices 102, 104, and 106 can be implantable devices or external devices that may provide one or more of the following functions with respect to a patient: (1) sensing, (2) data analysis, and (3) therapy. For example, in one embodiment, devices 102, 104, and 106 are either implanted or external devices used to measure a variety of physiological, subjective, and environmental conditions of a patient using electrical, mechanical, and/or chemical means. The devices 102, 104, and 106 can be configured to automatically gather data or can require manual intervention by the patient. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, devices 102, 104, and 106 also provide therapy. Therapy can be provided automatically or in response to an external communication. Devices 102, 104, and 106 are programmable in that the characteristics of their sensing, therapy (e.g., duration and interval), or communication can be altered by communication between the devices 102, 104, and 106 and other components of the advanced patient management system 100. Devices 102, 104, and 106 can also perform self-checks or be interrogated by the communication system 110 to verify that the devices are functioning properly. Examples of different embodiments of the devices 102, 104, and 106 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of an implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of a sensor in an implantable device. During the respiratory cycle, large volumes of air pass into and out of the body. The electrical resistance of the thorax changes markedly as a result of large differences in conductivity of air and body tissues. The thoracic resistance can be measured during respiration and corverted into a measurable electrical signal (i.e., impedance) so that breathing rate and profile can be approximated. Implantable devices can also sense chemical conditions, such as glucose levels. blood oxygen levels, etc. Further, the advanced patient management system 100 may utilize other implantable devices as well that provide physiological measurements of the patient, such as drug pumps, neurological devices (e.g., stimulators), oxygen sensors, etc.

Derived measurements can also be determined from the implantable device sensors. For example, a sleep sensor can rely on measurements taken by an implanted accelerometer that measures body activity levels. The sleep sensor can estimate sleeping patterns based on the measured activity levels. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 102, 104, and 106 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Devices 102, 104, and 106 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 102, 104, and 106 (for example, device 106) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge with a finer resolution than the quanta of the three responses.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 106 can be any device that accepts input from a patient or other concerned individual and/or provides information in a format that is recognizable to the patient. Device 106 typically includes a keypad, mouse, display, handheld device, interactive TV, cellular telephone or other radio frequency ("RF") communications device, cordless phone, corded phone, speaker, microphone, email message, or physical stimulus.

Figure 2:
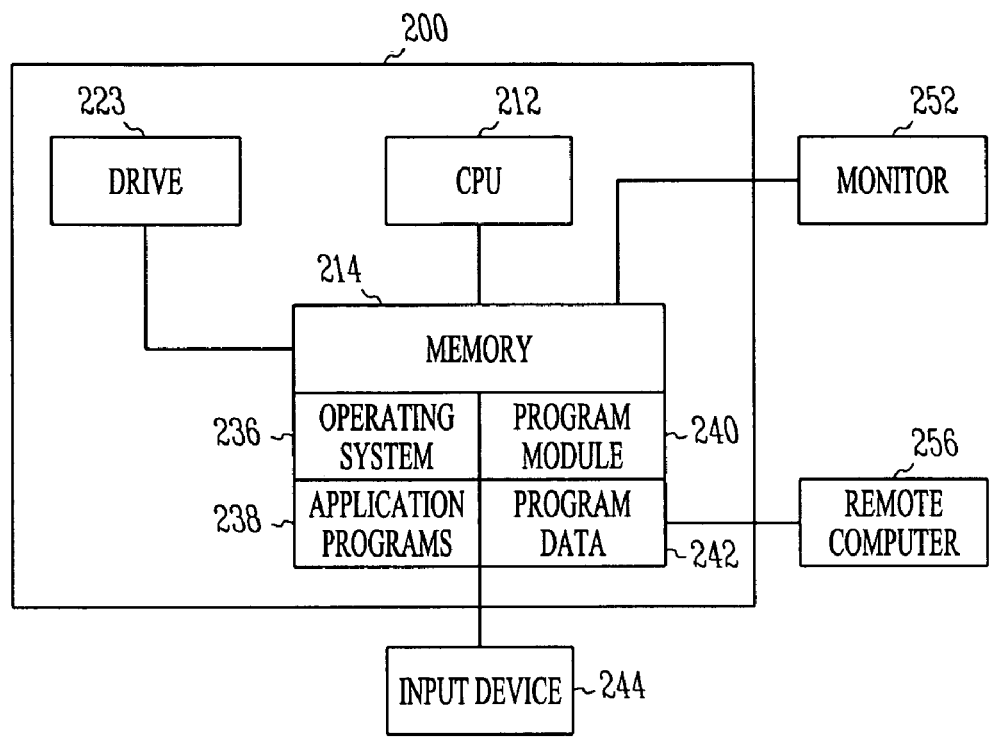
FIG. 2 illustrates an example computer system for use with the advanced patient management system.

In one example embodiment, the subjective device 106 includes or is part of a computer system 200, as illustrated in FIG. 2. The example computer system 200 includes a central processor unit 212 and a system memory 214. The computer system 200 further includes one or more drives 223 for reading data from and writing data to, as well as an input device 244, such as a keyboard or mouse, and a monitor 252 or other type of display device. A number of program modules may be stored on the drive 223, including an operating system 236, one or more application programs 238, other program modules 240, and program data 242. The computer system 200 can operate in a networked environment using logical connections to one or more remote computers or computer systems 256. Computer system 200 can also include hand-held computers such as a PDA computer.

The advanced patient management system 100 may also include one or more remote peripheral devices 109. The remote peripheral device 109 may include, for example and without limitation, cellular telephones, pagers, PDA devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well-being.

II. Interrogator/Transceiver Unit

Figure 3:
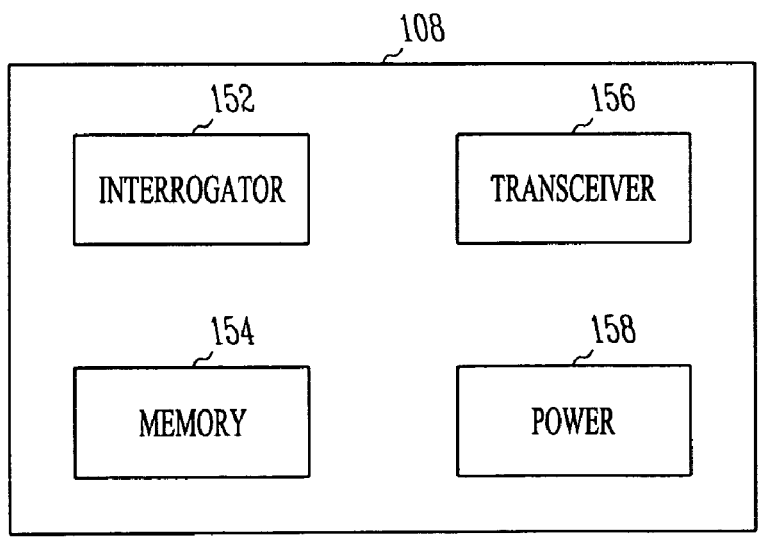
FIG. 3 illustrates an example interrogator/transceiver unit for use with the advanced patient management system.

Referring now to FIG. 3, the example advanced patient management system 100 includes one or more interrogator/transceiver units ("ITUs"), such as ITU 108. The ITU 108 includes an interrogator module 152 for sending and receiving data from a device, such as devices 102, 104, and 106, a memory module 154 for storing data, and a transceiver module 156 for sending and receiving data to and from other components of the APM system 100. The transceiver module may also operate as an interrogator of the devices 102, 104 and 106. The ITU 108 also includes a power module 158 that provides power.

The ITU 108 may perform one or more of the following functions: (1) data storage; (2) data analysis; (3) data forwarding; (4) patient interaction; (5) patient feedback; and (6) data communications. For example, the ITU 108 may facilitate communications between the devices 102, 104, and 106 and the communication system 110. The ITU 108 can, periodically or in real-time, interrogate and download into memory clinically relevant patient data from the devices 102, 104, and/or 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data is sent to the ITU 108 by the devices 102, 104, and 106 in realtime or periodically uploaded from buffers in the devices.

The ITU 108 may also allow patient interaction. For example, the ITU 108 may include a patient interface and allow the patient to input subjective data. In addition, the ITU 108 may provide feedback to the patient based on the data that has been analyzed or based on information communicated by the communication system 110.

In another embodiment, the ITU 108 includes a telemetry link from the devices to a network that forms the basis of a wireless LAN in the patient's home. The ITU 108 systematically uploads information from the devices 102, 104, and/or 106 while the patient is sleeping, for example. The uploaded data is transmitted through the communication system 110 or directly to the host 112. In addition, in one embodiment the ITU 108 functions in a hybrid form, utilizing wireless communication when available and defaulting to a local wireless portal or a wired connection when the wireless communication becomes unavailable.

Some devices, such as legacy implanted cardiac rhythm management ("CRM") devices, communicate via an internal telemetry transceiver that communicates with an external programmer. The communication range of such devices is typically 1 to 4 inches. ITU 108 may include a special short-range interrogator that communicates with a legacy device.

When the interrogator 152 uses radio frequency to communicate with the devices 102, 104, 106, the ITU 108 may be in the form of a small device that is placed in an inconspicuous place within the patient's residence. Alternatively, the ITU 108 may be implemented as part of a commonly-used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 108 may comprise a hand-held device such as a PDA, cellular telephone, or other similar device that is in wireless communication with the devices 102, 104, and 106. The hand-held device may upload the data to the communication system 110 wirelessly. Alternatively, the hand-held device may periodically be placed in a cradle or other similar device that is configured to transmit the data to the communication system 110.

In one embodiment, the ITU 108 can perform analysis on the data and provide immediate feedback, as well as perform a variety of self-diagnostic tests to verify that it is functioning properly and that communication with the communication system 110 has not be compromised. For example, the ITU 108 can perform a diagnostic loop-back test at a time set by the host 112, which involves sending a request through the communication system 110 to the host 112. The host 112 can then reply with a response back through the communication system 110 to the ITU 108. If a specific duration elapses before the ITU 108 receives the response or the ITU 108 receives an unexpected response, or if the host 112 does not receive the diagnostic test communication, the ITU 108 can provide indications that the system is not functioning properly and the host 112 can alert an operator that there may be compromised communications with that specific ITU 108. For example, if wireless communications between the ITU 108 and the communication system 110 have been interrupted, and the ITU 108 performs a self-diagnostic test that fails, the ITU 108 may alert the patient so that corrective action may be taken. The alert can take the form of a sound or a visual and/or audible annunciator to alert the patient that communication has been interrupted. In another embodiment, the ITU 108 can automatically fail-back to a wired system to communicate with the communication system 110 and perform the same communications compromise checks.

In other embodiments of the advanced patient management system 100, the ITU 108 function can be integrated into devices 102, 104, and 106, so that the devices can communicate directly with the communication system 110 and/or host 112. The devices 102, 104 and 106 can incorporate multi-mode wireless telecommunications such as cellular, BLUETOOTH, or IEEE 802.11 B to communicate with the communication system 110 directly or through a local wireless to a wired portal in the patients' home. For example, device 102 may include a miniature cellular phone capable of wirelessly uploading clinical data from the device on a periodic basis. This is particularly advantageous for devices that are mobile (e.g., an implanted device in a patient that is traveling).

To conserve the energy of the devices 102, 104, and 106, particularly when the devices (e.g., device 102) are configured to communicate directly with the communication system 110 without using an ITU 108, in one example embodiment the devices are configured to communicate during a given duty cycle. For example, the device 102 can be configured to communicate with the communication system 110 at given intervals, such as once a week. The device 102 can record data for the time period (e.g., a week) and transmit the data to the communication system 110 during the portion of the cycle that transmission is active and then conserve energy for the rest of the cycle. In another example, the device 102 conserves energy and only communicates with the communication system 110 when an "interesting" event, such as a heart arrhythmia, has occurred. In this manner, device 102 can communicate directly with the communication system 110 and/or host 112 without requiring an ITU 108, while conserving the energy of the device by communicating only during a given duty cycle.

The interrogation rate of the ITU 108 can be varied depending on disease state and other relevant factors. In addition, the devices 102, 104, and 106 can be configured to "wake up" frequently (e.g., once every couple minutes) to provide the ITU 108 an access window for the ITU 108 to provide commands to the devices 102, 104, and 106, as well as upload data from the devices.

If multiple devices, Such as devices 102, 104, and 106, are provided for a given patient, each device may include its own means for communicating with the ITU 108 or communication system 110. Alternatively, a single telemetry system may be implemented as part of one of the devices, or separate from the devices, and each device 102, 104, and 106 can use this single telemetry system to communication with the ITU 108 or the communication system 110.

In yet another embodiment, the devices 102, 104, and 106 include wires or leads extending from devices 102, 104, and 106 to an area external of the patient to provide a direct physical connection. The external leads can be connected, for example, to the ITU 108 or a similar device to provide communications between the devices 102, 104, and 106 and the other components of the advanced patient management system 100.

The advanced patient management system 100 can also involve a hybrid use of the ITU 108. For example, the devices 102, 104, and 106 can intelligently communicate via short-range telemetry with the ITU when the patient is located within the patient's home and communicate directly with the communication system 110 or host 112 when the patient is traveling. This may be advantageous, for example, to conserve battery power when the devices are located near an ITU.

III. Communication System

Figure 4:
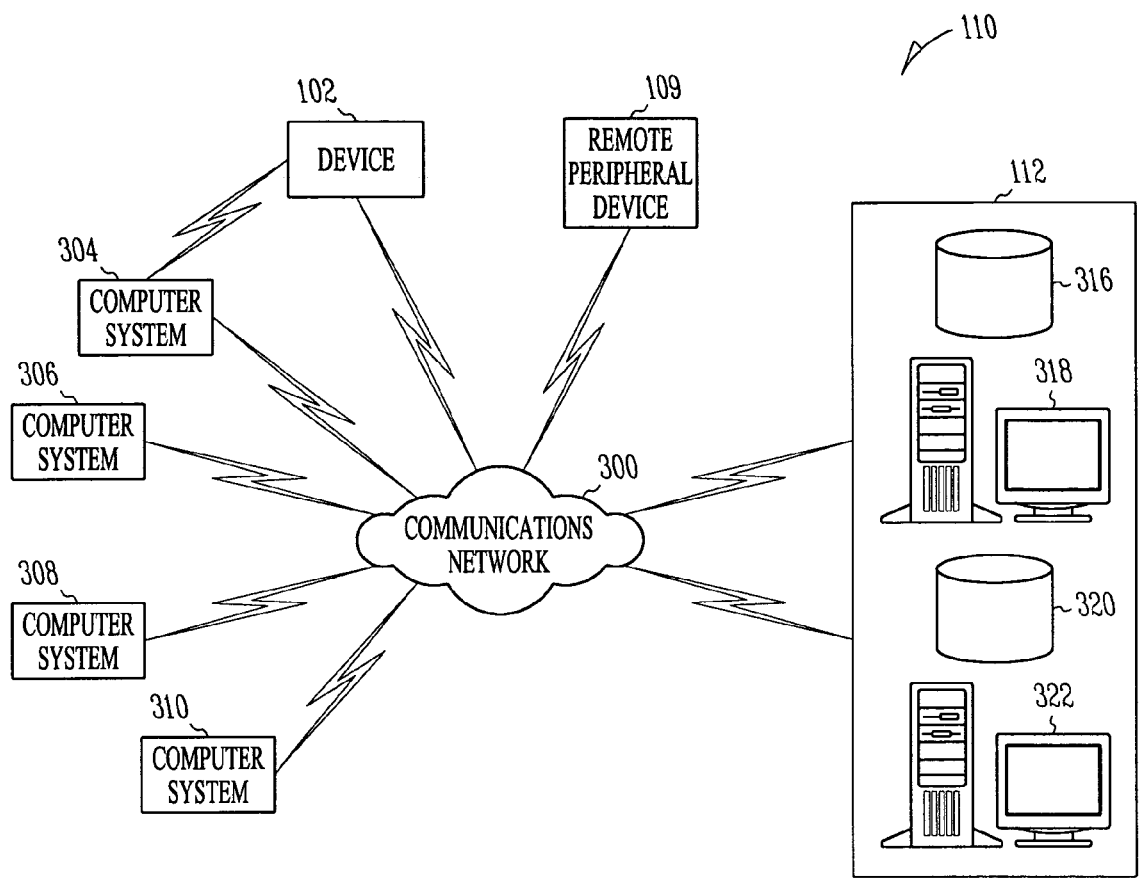
FIG. 4 illustrates an example communication system for use with the advanced patient management system.

Communication system 110 provides for communications between and among the various components of the advanced patient management system 100, such as the devices 102, 104, and 106, host 112, and remote peripheral device 109. FIG. 4 illustrates one embodiment for the communication system 110. The communication system 110 includes a plurality of computer systems 304, 306, 308, and 310, as well as device 102, host 112, and remote peripheral device 109, connected to one another by the communications network 300. The communications network 300 may be, for example, a local area network (LAN), wide area network (WAN), or the Internet. Communications among the various components, as described more fully below, may be implemented using wired or wireless technologies.

In the example embodiment illustrated, the host 112 includes server computers 318 and 322 that communicate with computers 304, 306, 308, and 310 using a variety of communications protocols, described more fully below. The server computers 318 and 322 store information in databases 316 and 320. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, timehopping, frequency hopping, SMTP, FTP, and TCP/IP may be used. Other proprietary methods and protocols may also be used. Further, a combination of two or more of the communication methods and protocols may also be used.

The various communications between the components of the advanced patient management system 100 may be made secure using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

Communications among the various components of the advanced patient management system 100 may be enhanced using compression techniques to allow large amounts of data to be transmitted efficiently. For example, the devices 102, 104, and 106 or the ITU 108 may compress the recorded information prior to transmitting the information to the ITU 108 or directly to the communication system 110.

The communication methods and protocols described above can facilitate periodic and/or real-time delivery of data.

IV. Host

The example host 112 includes a database module 114, an analysis module 116, and a delivery module 118 (see FIG. 1). Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patient's information the host 112 is receiving at a given instant. Alternatively, each device 102, 104, and 106 may be assigned a unique identification number, or a unique patient identification number may be transmitted with each transmission of patient data.

When a device is first activated, several methods may be used to associate data received by the advanced patient management system 100 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 1, the example database module 114 includes a patient database 400, a population database 402, a medical database 404, and a general database 406, all of which are described further below.

The patient database 400 includes patient specific data, including data acquired by the devices 102, 104, and 106. The patient database 400 also includes a patient's medical records. The patient database 400 can include historical information regarding the devices 102, 104, and 106. For example, if device 102 is an implantable cardioverter defibrillator (ICD), the patient database 400 records the following device information: P and R measurements, pacing frequency, pacing thresholds, shocking events, recharge time, lead impedance, battery voltage/remaining life, ATR episode and EGMs, histogram information, and other device-specific information. The information stored in the database 400 can be recorded at various times depending on the patient requirements or device requirements. For example, the database 400 is updated at periodic intervals that coincide with the patient downloading data from the device. Alternatively, data in the database 400 can be updated in real time. Typically, the sampling frequency depends on the health condition being monitored and the co-morbidities.

The population database 402 includes non-patient specific data, such as data relating to other patients and population trends. The population database 402 also records epidemic class device statistics and patient statistics. The population database 402 also includes data relating to staffing by health care providers, environmental data, pharmaceuticals, etc.

The example medical database 404 includes clinical data relating to the treatment of diseases. For example, the medical database 404 includes historical trend data for multiple patients in the form of a record of progression of their disease(s) along with markers of key events.

The general database 406 includes non-medical data of interest to the patient. This can include information relating to news, finances, shopping, technology, entertainment, and/or sports. The general database 406 can be customized to provide general information of specific interest to the patient. For example, stock information can be presented along with the latest health information as detected from the devices 102, 104, and 106.

In another embodiment, information is also provided from an external source, such as external database 600. For example, the external database 600 includes external medical records maintained by a third party, such as drug prescription records maintained by a pharmacy, providing information regarding the type of drugs that have been prescribed for a patient.

The example analysis module 116 includes a patient analysis module 500, device analysis module 502, population analysis module 504, and learning module 506.

Patient analysis module 500 may utilize information collected by the advanced patient management system 100, as well as information for other relevant sources, to analyze data related to a patient and provide timely and predictive assessments of the patient's wellbeing. In performing this analysis, the patient device module 500 may utilize data collected from a variety of sources, include patient specific physiological and subjective data collected by the advanced patient management system 100, medical and historical records (e.g., lab test results, histories of illnesses, etc., drugs currently and previously administered, etc.), as well as information related to population trends provided from sources external to the advanced patient management system 100.

For example, in one embodiment, the patient analysis module 500 makes a predictive diagnosis of an oncoming event based on information stored in the database module 114. For example, the data continuously gathered from a device of a given patient at a heightened risk for a chronic disease event (such as de-compensations in heart failure) is analyzed. Based on this analysis, therapy, typically device-based or pharmaceutical, is then be applied to the patient either through the device or through clinician intervention.

In another example embodiment, the patient analysis module 500 provides a diagnosis of patient health status and predicted trend based on present and recent historical data collected from a device as interpreted by a system of expert knowledge derived from working practices within clinics. For example, the patient analysis module 500 performs probabilistic calculations using currently-collected information combined with regularly-collected historical information to predict patient health degradation.

In another example embodiment, the patient analysis module 500 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 500 may also provide means for periodic processing of present and historical data to yield a multidimensional health state indication along with disease trend prediction, next phase of disease progression co-morbidities, and inferences about what other possible diseases may be involved. The patient analysis module 500 may also integrate data collected from internal and external devices with subjective data to optimize management of overall patient health.

Device analysis module 502 analyzes data from the devices 102, 104, and 106 and ITU 108 to predict and determine device issues or failures. For example, if an implanted device 102 fails to communicate at an expected time, device analysis module 502 determines the source of the failure and takes action to restore the performance of the device 102. The device analysis module 502 may also perform additional deterministic and probabilistic calculations. For example, the device analysis module 502 gathers data related to charge levels within a given device, such as an ICD, and provides analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

Population analysis module 504 uses the data collected in the database module 114 to manage the health of a population. For example, a clinic managing cardiac patients can access the advanced patient management system 100 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 504 trends the patient population therapy and management as recorded by the devices and directs health care resources to best satisfy the needs of the population. The resources can include people, facilities, supplies, and/or pharmaceuticals. In other embodiments, the population analysis module detects epidemics and other events that affect large population groups. The population analysis module 504 can issue alerts that can initiate a population quarantine, redirect resources to balance size of staffing with number of presenting population, and predict future need of qualified specialists.

The population analysis module 504 may utilize a variety of characteristics to identify like-situated patients, such as, for example, sex, age, genetic makeup, etc. The population analysis module 504 may develop large amounts of data related to a given population based on the information collected by the advanced patient management system 100. In addition, the population analysis module 504 may integrate information from a variety of other sources. For example, the population analysis module 504 may utilize data from public domain databases (e.g., the National Institute of Health), public and governmental and health agency databases, private insurance companies, medical societies (e.g., the American Heart Association), and genomic records (e.g., DNA sequences).

In one embodiment, the host 112 may be used as a "data clearinghouse," to gather and integrate data collected from the devices 102, 104, and 106, as well as data from sources outside the advanced patient management system 100. The integrated data can be shared with other interested entities, subject to privacy restrictions, thereby increasing the quality and integration of data available.

Learning module 506 analyzes the data provided from the various information sources, including the data collected by the advanced patient system 100 and external information sources. For example, the learning module 506 analyzes historical symptoms, diagnoses, and outcomes along with time development of the diseases and co-morbidities. The learning module 506 can be implemented via a neural network (or equivalent) system.

The learning module 506 can be partially trained (i.e., the learning module 506 may be implemented with a given set of preset values and then learn as the advanced patient management system functions) or untrained (i.e., the learning module 506 is initiated with no preset values and must learn from scratch as the advanced patient management system functions). In other alternative embodiments, the learning module 506 may continue to learn and adjust as the advanced patient management system functions (i.e., in real time), or the learning module 506 may remain at a given level of learning and only advanced to a higher level of understanding when manually allowed to do so.

In a neural network embodiment, new clinical information is presented to create new neural network coefficients that are distributed as a neural network knowledge upgrade. The learning module 506 can include a module for verifying the neural network conclusions for clinical accuracy and significance. The learning module can analyze a database of test cases, appropriate outcomes and relative occurrence of misidentification of the proper outcomes. In some embodiments, the learning module 506 can update the analysis module 116 when the analysis algorithms exceed a threshold level of acceptable misidentifications.

The example learning module 506 uses various algorithms and mathematical modeling such as, for example, trend and statistical analysis, data mining, pattern recognition, cluster analysis, neural networks and fuzzy logic. Learning module 506 may perform deterministic and probabilistic calculations. Deterministic calculations include algorithms for which a clear correlation is known between the data analyzed and a given outcome. For example, there may be a clear correlation between the energy left in a battery of an implantable device and the amount of time left before the battery must be replaced.

A probabilistic calculation involves the correlation between data and a given outcome that is less than 100 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 506 performs probabilistic calculations and selects a given response based on less than a 100% probability. Further, as the learning module 506 "learns" for previous determinations (e.g., through a neural network configuration), the learning module 506 becomes more proficient at assigning probabilities for a given data pattern, thereby being able to more confidently select a given response. As the amount of data that has been analyzed by the learning module 506 grows, the learning module 506 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 506 is capable of tracking and forecasting a patient's clinical status with increasing levels of sophistication by measuring a number of interacting co-morbidities, all of which may serve individually or collectively to degrade the patient's health. This enables learning module 506, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

Delivery module 118 coordinates the delivery of feedback based on the analysis performed by the host 112. In response to the analysis module 116, delivery module 118 can manage the devices 102, 104, and 106, perform diagnostic data recovery, program the devices, and otherwise deliver information as needed. In some embodiments, the delivery module 118 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif. A patient can access his or her My Yahoo homepage and receive information regarding current health and trends derived from the information gathered from the devices 102, 104, and 106, as well as other health information gathered from other sources. The patient may also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 100, as well as any analysis performed by the system 100, is delivered by delivery module 118 to a caregiver's hospital computer system for access by the caregiver. A standard or custom interface facilitates communication between the advanced patient management system 100 and a legacy hospital system used by the caregiver so that the caregiver can access all relevant information using a system familiar to the caregiver.

The advanced patient management system 100 can also be configured so that various components of the system (e.g., ITU 108, communication system 110, and/or host 112) provide reporting to various individuals (e.g., patient and/or caregiver). For example, different levels of reporting can be provided by (1) the ITU 108 and (2) the host 112. The ITU 108 may be configured to conduct rudimentary analysis of data gathered from devices 102, 104, and 106, and provide reporting should an acute situation be identified. For example, if the ITU 108 detects that a significant heart arrhythmia is imminent or currently taking place, the ITU 108 provides reporting to the patient in the form of an audible or visual alarm.

The host 112 can provide a more sophisticated reporting system. For example, the host 112 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the advanced patient management system 100, the delivery module 118 can communicate directly with the devices 102, 104, and 106, contact a pharmacy to order a specific medication for the patient, and/or contact 911 emergency response. In an alternative embodiment, the delivery module 118 and/or the patient may also establish a voice communication link between the patient and a caregiver, if warranted.

In addition to forms of reporting including visual and/or audible information, the advanced patient management system 100 can also communicate with and reconfigure one or more of the devices 102, 104, and 106. For example, if device 102 is part of a cardiac rhythm management system, the host 112 can communicate with the device 102 and reconfigure the therapy provided by the cardiac rhythm management system based on the data collected from one or more of the devices 102, 104, and 106. In another embodiment, the delivery module 118 can provide to the ITU 108 recorded data, an ideal range for the data, a conclusion based on the recorded data, and a recommended course of action. This information can be displayed on the ITU 108 for the patient to review or made available on the peripheral device 109 for the patient and/or clinician to review.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

V. Device Communications

Figure 5:
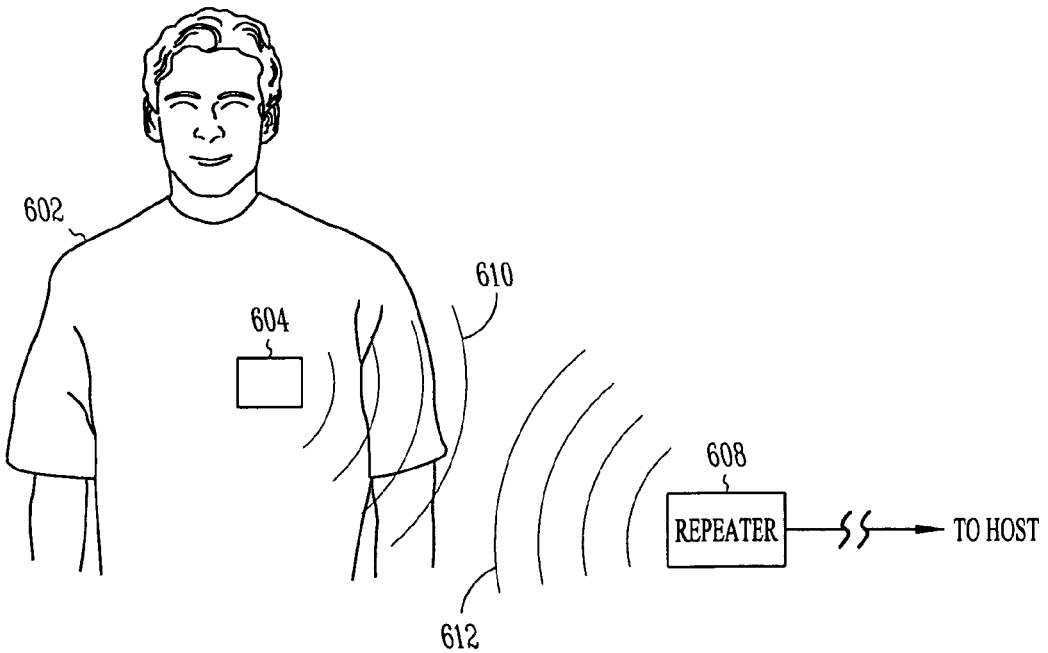
FIG. 5 illustrates communication between an implantable medical device and an external unit according to one embodiment of the present invention.

FIG. 5 illustrates bi-directional communication between the implantable medical device (implant) 604 and an external unit 608 Such as a repeater type of ITU 108 discussed above. The implant 604 is located within the body of the patient 602 and communicates with the external unit 608 through RF signaling. RF signals 610 are transmitted by the implant 604 and are received by the external unit 608. Likewise, RF signals 612 are transmitted by the external unit 608 and are received by the implant 604. The external unit may also be in communication with a host system, such as the advanced patient management system discussed above.

Figure 6:
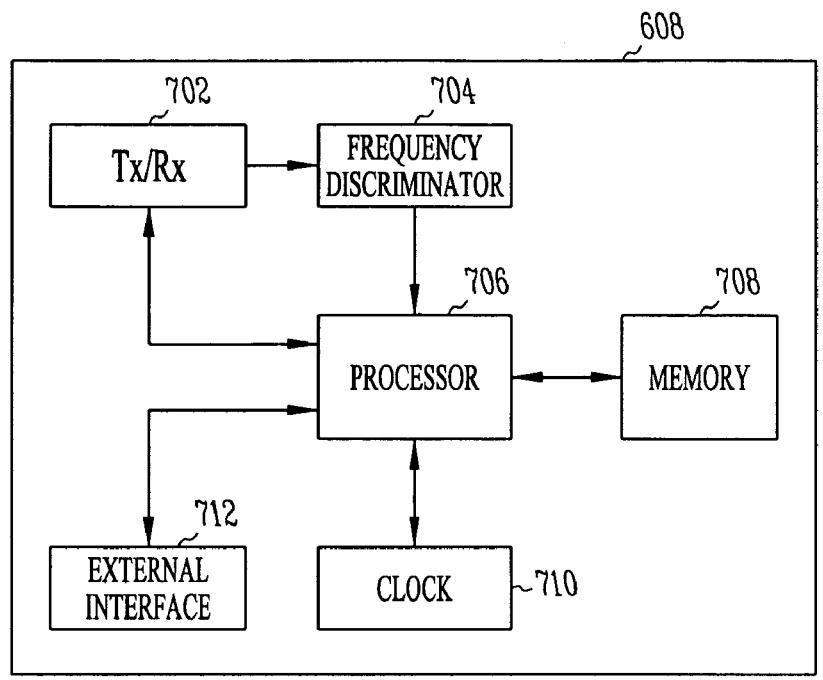
FIG. 6 illustrates components of an exemplary external unit such as the external unit of FIG. 5 according to one embodiment of the present invention.

As shown in FIG. 6, the external unit 608 has several main components that are utilized when establishing communications. The external unit 608 includes a transmitter/receiver 702 which may be a transceiver or separate transmitter and receiver devices. The transmitter/receiver 702 may provide full-duplex and/or half-duplex communications with the implant 604. The transmitter/receiver 702 transmits the RF signals when instructed by a processor 706. The processor 706 orchestrates a communication protocol by controlling the transmitter/receiver 702 as discussed below. The processor 706 also provides the data to the transmitter/receiver 702 so that the transmitter/receiver can encode the RF signals with the data through various means known in the art for wireless data transfer.

The transmitter/receiver 702 also receives RF signals that include data sent by the implant 604. The transmitter/receiver 702 recovers the data from the RF signal and passes the data to the processor 706. The transmitter/receiver 702 also passes the RF signal to a frequency discriminator 704. The frequency discriminator 704 compares the frequency of the RF signal (i.e., carrier frequency) to a reference frequency used as the carrier by the transmitter section and/or receiver section of transmitter/receiver 702. The frequency discriminator 704 passes the difference resulting from the comparison to the processor 706 which can then alter the frequency of the transmitter section and/or receiver section of transmitter/receiver 702 by the difference.

The processor 706 communicates with a memory 708 generally comprised of RAM and ROM when implementing the communications protocols. Furthermore, the processor 706 may perform additional tasks in some embodiments, such as limited analysis of the data received from the implant 606 which involves passing data to and from the memory 708. As discussed below, the communications between the external unit 608 and the implant 604 occur on a time schedule to conserve battery life and a clock 710 provides the time to the processor 706 so that the time schedule can be followed. The processor 706 may also communicate with an external interface 712, such as a modem, so that the external unit 608 can communicate with the host system.

The transmitter/receiver 702 may operate at multiple channels for both the transmit section and the receive section. Additionally, the transmitter/receiver 702 has transmit and receive center frequencies for each channel that are adjustable in response to commands from the processor 706. The transmitter/receiver 702 may employ frequency synthesizers to produce the multiple channels and the variation of center frequency. As discussed below, the external unit 608 learns the center frequencies of the transmission and reception of the implant 604 each time communication is established to account for frequency uncertainty, and the external unit 608 adapts the center frequency of the appropriate transmit and receive channels for optimized communication with the implant 604.

Figure 7:
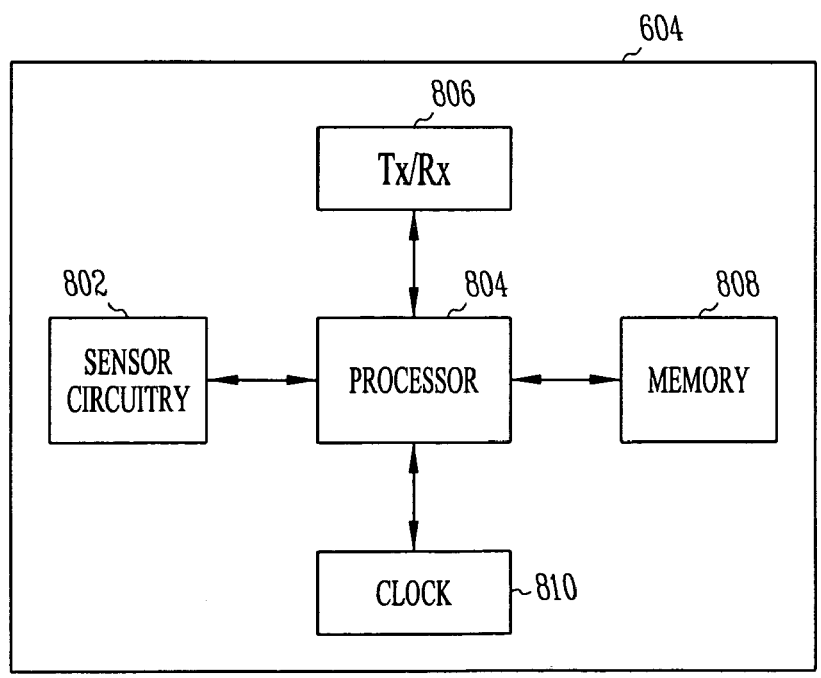
FIG. 7 illustrates components of an exemplary implantable medical device according to one embodiment of the present invention.

The components of one embodiment of the implant 604 are shown in FIG. 7. In this embodiment, the implant 604 has a transceiver 806 that transmits signals on a transmit frequency and receives signals on a receive frequency. The transmit frequency and receive frequency are separated in frequency by a fixed amount and may be produced by a surface acoustic wave (SAW) based transceiver 806. The particular transmit and receive frequencies remain uncertain, but the fixed separation is always assumed to be constant regardless of the degree of uncertainty. This fixed separation is known by the external unit 608 and may be stored in memory 708 of the external unit 608.

The transceiver 806 encodes data received from a processor 804 for transmission through the RF signals. The transceiver 806 also recovers data from the RF signals that are received and passes the data to the processor 804. The processor also communicates with memory 808, typically including RAM and ROM, as well as an internal clock 810. The processor 804 interacts with the memory 808 when implementing the communications protocols and when performing additional tasks such receiving information from or configuring sensor circuitry 802. The internal clock 810 provides the time information to the processor 804 that allows the processor 804 to follow the time schedule for establishing periodic communications with the external unit 608.

The sensor circuitry 802 includes one or more of the various sensors discussed above, Such as but not limited to cardiac sensing, pacing, defibrillator, and electrogram circuitry. The processor 804 may perform various functions in relation to the sensor circuitry 802 in addition to controlling the communications protocol. For example, the processor 804 may analyze sensor data and adapt sensor circuitry 802 based on the analysis.

Figure 8:
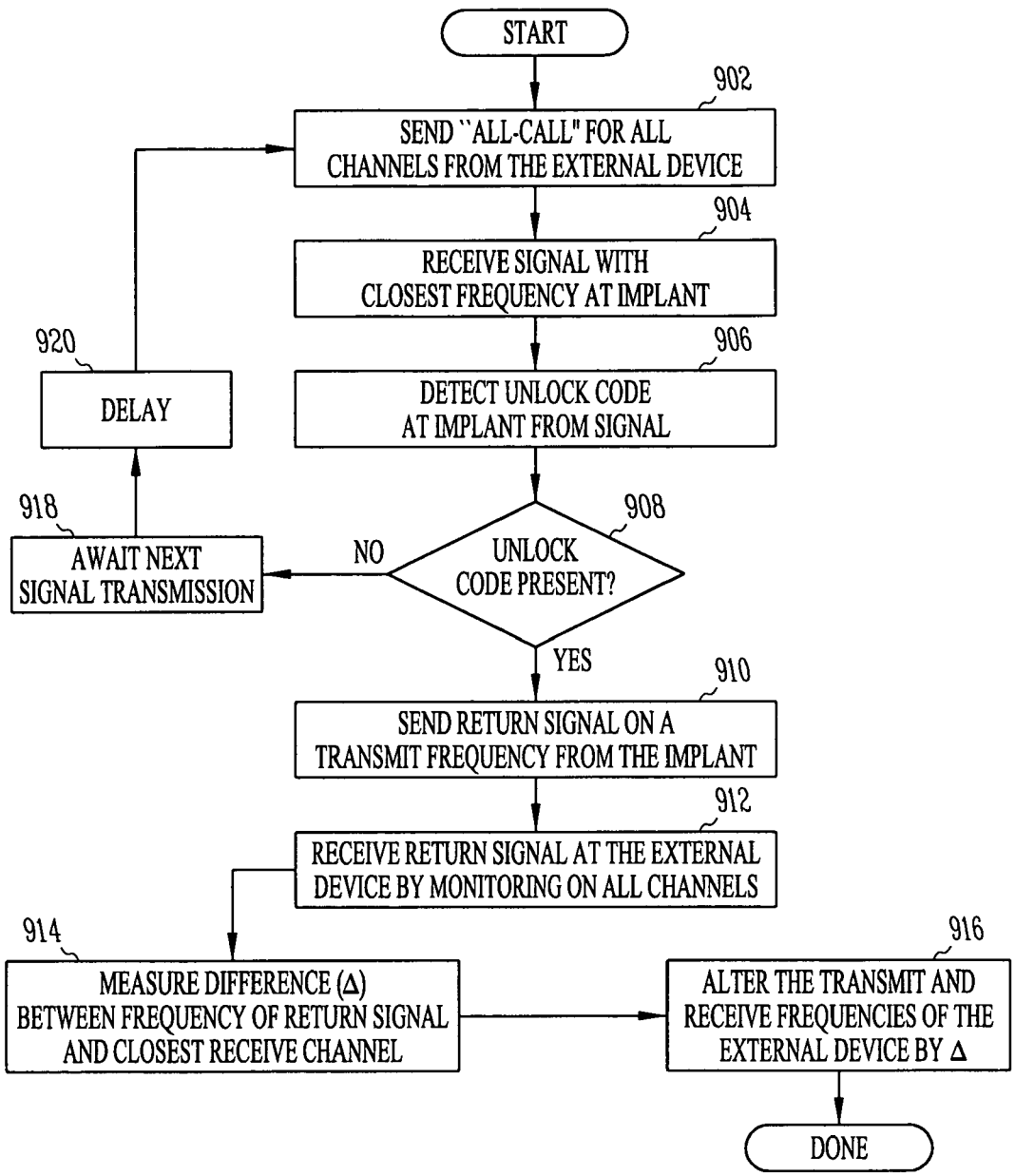
FIG. 8 illustrates an exemplary operational flow of a communication protocol between the external unit and implantable medical device according to one embodiment of the present invention.

An exemplary operational flow of the communication protocol between the external unit 608 and the implant 604 is shown in FIG. 8 and applies where the implant 604 has the fixed differential between its transmit and receive frequencies. The logical operations of FIG. 8 are generally performed by the processor 706 of external unit 608 and the processor's interaction with the transmitter/receiver 702 and frequency discriminator 704, as well as the processor 804 and its interaction with transmitter/receiver 806. The logical operations of FIG. 8 as well as the various other embodiments of the present invention are implemented (1) as a sequence of computer implemented acts or program modules running on a computing system of the external unit 608 and implant 604 and/or (2) as interconnected machine logic circuits or circuit modules within the computing systems. The implementation is a matter of choice dependent on the performance requirements of the computing system implementing the invention. Accordingly, the logical operations making up the embodiments of the present invention described herein are referred to variously as operations, acts or modules. It will be recognized by one skilled in the art that these operations, acts, and modules may be implemented in software, in firmware, in special purpose digital logic, and any combination thereof without deviating from the spirit and scope of the present invention as recited within the claims attached hereto.

Figure 9:
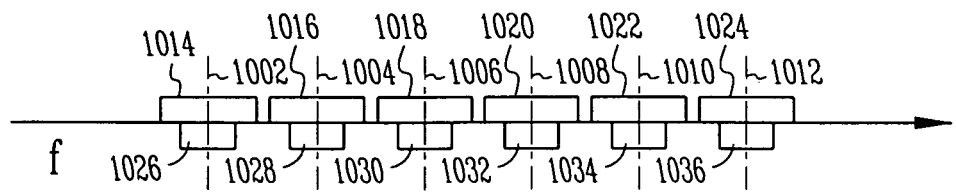
FIG. 9 illustrates an all-call signal across multiple channels produced by the external unit according to one embodiment of the present invention.

The process starts by the external unit 608 sending an all-call signal at an appropriate time for establishing communications at send operation 902. The all-call signal is used where the external unit is capable of communicating with implants on a variety of channels, but it is not known exactly which channel the implant 604 receives on. FIG. 9 shows an example of an all-call signal.

In this example of FIG. 9, the possible channels for communicating have center frequencies 1002, 1004, 1006, 1008, 1010, and 1012. One channel with the center frequency 1002 has a normal bandwidth 1014. Similarly, the other channels have bandwidths 1016, 101 8, 1020, 1022, and 1024. During the all-call signal, the external unit 608 transmits on all available channels, but utilizes a signal having a bandwidth much narrower than the normal bandwidth availability per channel. As can be seen, the all-call signal has bandwidths 1026, 1028, 1030, 1032, 1034, and 1036 for each of the channels.

Figure 10:
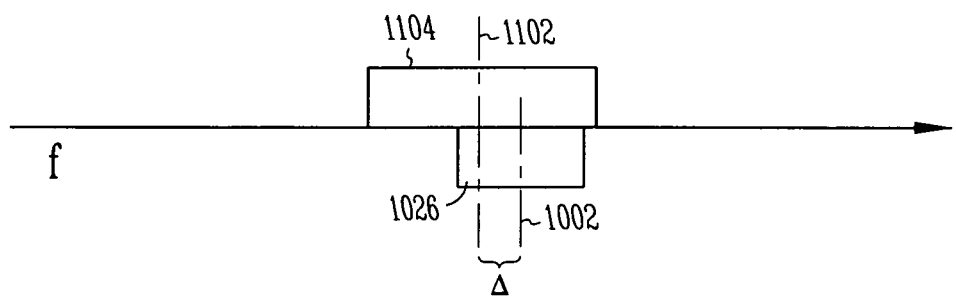
FIG. 10 illustrates a reception by the implantable medical device of one signal of the all-call signal.

The all-call bandwidths are sufficiently narrow so that if the center frequency of transmission by the external unit 608 does not precisely match the center frequency of reception by the implant 604, then the signal still falls within the normal bandwidth of reception of the implant 604. An example of this is shown in FIG. 10 where a center frequency 1102 is the center frequency for a receive channel being used by the implant 604. The transmission channel of the external unit 608 that matches the channel of reception for the implant 604 has a center frequency 1002. The signal from the all-call is centered on frequency 1002 and has a bandwidth of 1026. The center frequency of transmission 1002 differs from the center frequency of reception 1102 by $\Delta$. The narrow bandwidth 1026 compensates for the $\Delta$, and the signal falls within the reception bandwidth 1104 of the implant 604 enabling the implant 604 to receive the signal.

In this embodiment, the all-call signal includes an unlock code that tells a specific implant 604 to respond. This unlock code 604 prevents communication being established with an incorrect implant 604 when multiple implants are in proximity to the external unit 608. At receive operation 904 of FIG. 8, the implant 604 receives one of the signals of the all-call signal which has the closest frequency to the implant's receive channel as discussed in relation to FIG. 10. The implant 604 analyzes the signal to detect the proper unlock code at detect operation 906.

Query operation 908 of the implant tests whether the proper unlock code was detected. If it was not detected, then the implant 604 awaits the next signal transmission from the external unit 608 at wait operation 918. After a delay operation 920, where the external unit 608 may have stopped transmitting and begun listening for a return signal, operational flow returns to send operation 902. If query operation 908 finds that the proper unlock was detected, then operational flow transitions to send operation 910.

Send operation 910 sends a return signal on a transmit frequency from the implant 604. The return signal may also utilize a narrow bandwidth so that it falls within the bounds of a receive channel of the external Unit 608. The external unit 608 receives the return signal by monitoring on all available channels, either sequentially or simultaneously, at receive operation 912. Once the return signal has been received, the $\Delta$ between the return signal center frequency and the center frequency of the closest receive channel is determined with the frequency discriminator 704 at difference operation 914. The external unit 608 knows which transmit frequency to use for future communications based on the receive channel that obtained the return signal and stored associations between transmit and receive channels, such as in a look up table, or based on receive frequency data provided by the implant 604 in the return signal.

Once the $\Delta$ is known, the external unit 608 has learned the optimal location of the center channel for both transmitting to and receiving from the implant 604. At frequency operation 916, the transmit frequency and the receive frequency of the external unit 608 that is being utilized for communication with the implant 604 is altered by $\Delta$ to align the center frequency for the transmit and receive channels. Once the center frequencies have been aligned, full bandwidth bidirectional communication can occur without sidebands falling outside the normal allotted bandwidth for a particular channel. At this point, patient data, reprogramming instructions, and other information is passed between the implant 604 and the external unit 608, and then communication may be terminated.

Figure 11:
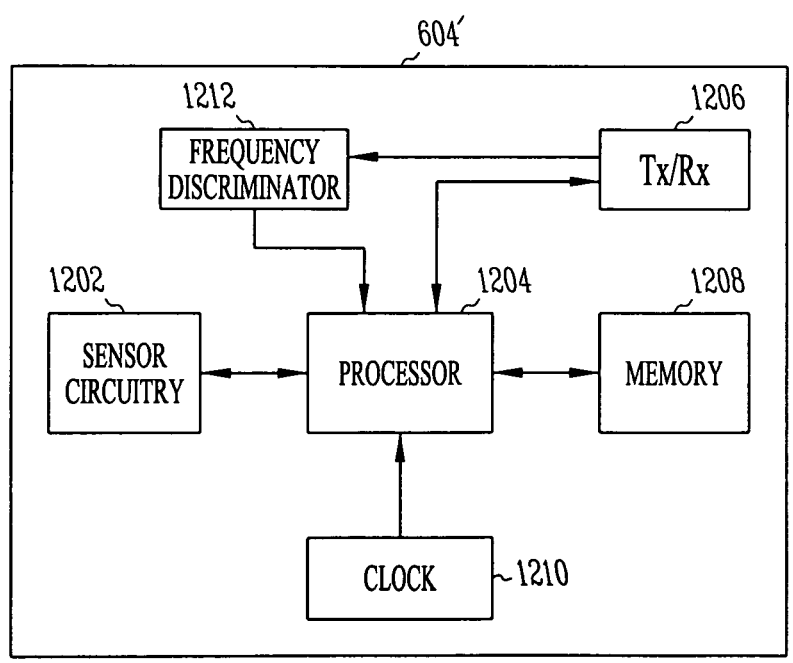
FIG. 11 illustrates components of another exemplary implantable medical device according to one embodiment of the present invention.

The components of an alternative implant 604' are shown in FIG. 11. These components also include a processor 1204 that communicates with the same sensor circuitry 1202, clock 1210, and memory 1208. However, in this embodiment, the implant 604' includes a transmitter/receiver section 1206 that contains a separate transmitter and receiver whose center frequencies are not separated by a fixed difference. Thus, there are separate uncertainties as to the transmit and receive frequencies.

To account for this additional uncertainty, this implant 604' includes a frequency discriminator 1212. The discriminator 1212 obtains the frequency of the signal received by the receiver section of transmitter/receiver 1206 and detects a difference $\Delta_1$ between the center frequency of the receive frequency and the center frequency of the received signal. The processor 1204 obtains $\Delta_1$ from the frequency discriminator and sends a $\Delta_1$ indication in a data packet back to the external unit 608 through the transmitter section of transmitter/receiver 1206. This indication may also contain an indication of the appropriate receive channel for which $\Delta_1$ is an error correction.

Figure 12:
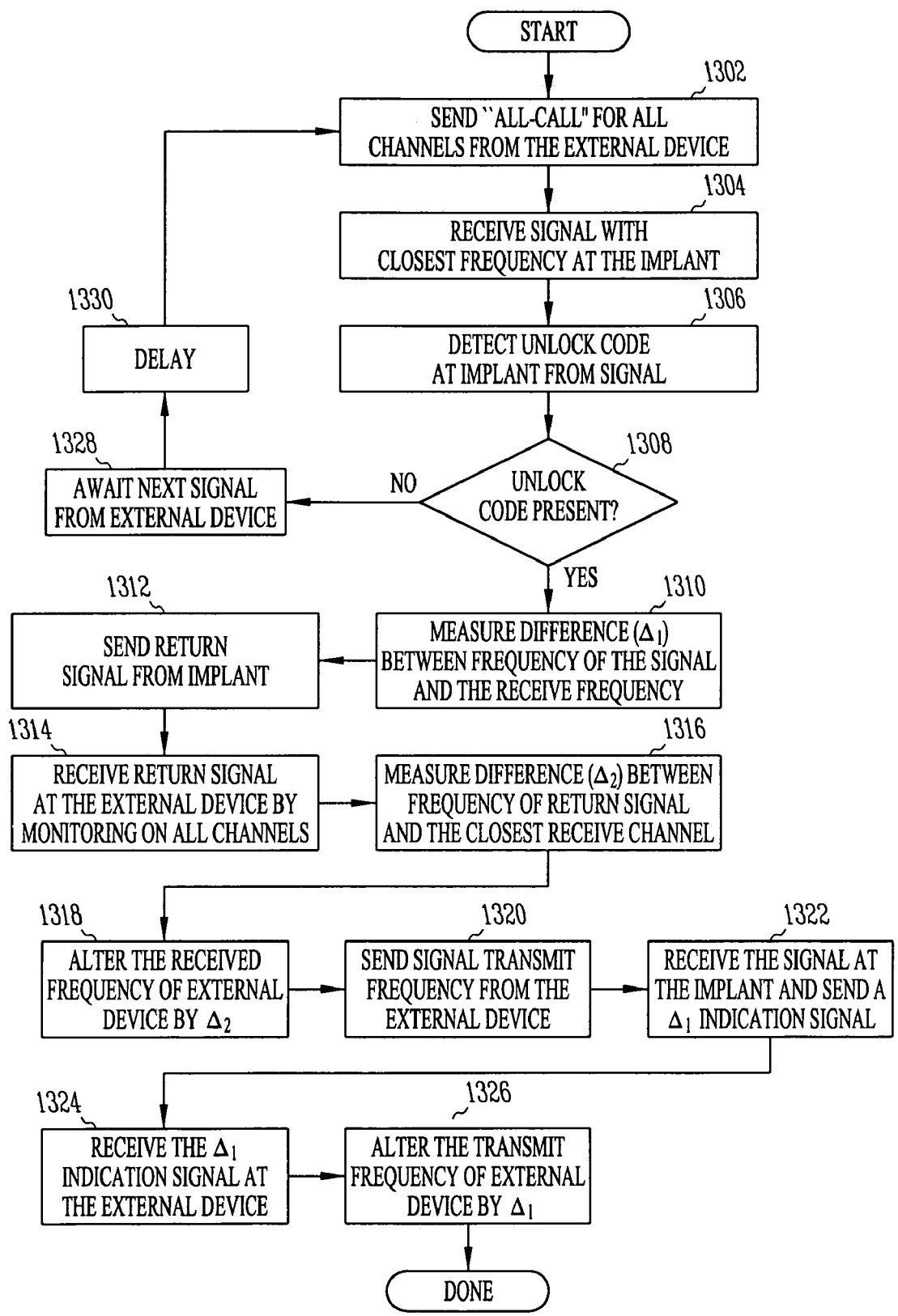
FIG. 12 illustrates another exemplary operational flow of a communication protocol between the external unit and the implantable medical device of FIG. 11 according to one embodiment of the present invention.

The operational flow of one communication protocol for addressing the separate transmit and receive uncertainties is shown in FIG. 12. As with the operational flow of FIG. 8, the process begins at send operation 1302 where an all-call is sent by the external unit 608. At receive operation 1304, the implant 604' receives the inbound signal having the center frequency closest to the center frequency of the receive channel. At detect operation, the implant 604' detects whether the proper unlock code is included in the received signal. Query operation 1308 tests whether the proper unlock code is present.

As occurred in FIG. 8, if the unlock code is not present, then the implant 604' waits for the next signal at wait operation 1328. After the delay 1330 of the external unit 608 pausing to listen for a return signal, operational flow returns to send operation 1302. If query operation 1308 finds that the proper unlock code was detected, then the difference $\Delta_1$ between the center frequency of the received signal and the center frequency of the receive channel is measured at difference operation 1310. The implant 604' then sends a return signal at its transmit frequency at send operation 1312.

The external unit 608 receives the return signal at receive operation 1314 by monitoring on all available receive channels, either simultaneously or sequentially. Once the return signal has been received, the external unit 608 measures the difference $\Delta_2$ between the center frequency of the return signal and the center frequency of the receive channel closest to the return signal at measure operation 1316. Once $\Delta_2$ is known, the external unit 608 alters the receive frequency of the channel closest to the return signal by $\Delta_2$ so that the receive channel has a center frequency that aligns with the center frequency of return signals transmitted by the implant 604'. The external unit 608 is now able to receive full bandwidth signals from the implant 604'.

After altering the receive frequency, at send operation 1320 the external unit 608 sends another signal. This signal is either another all-call or is at a specific transmit frequency that is known by association to the frequency of the return signal, such as by accessing a look-up table in memory 708. The specific transmit frequency, if known, corresponds to the receive frequency of the implant 604' but is likely to be offset again due to the receive frequency uncertainty of the implant 604' that is independent of the transmit frequency uncertainty of the implant 604'.

The implant 604' receives the signal which triggers the implant 604' to send another return signal that contains a data packet having an indication of $\Delta_1$. The external unit 608 receives the indication return signal at receive operation 1324, and the alters the center frequency of the transmit channel by $\Delta_1$. The center frequency of the transmit channel now aligns with the center frequency of the receive channel of the implant 604', and the implant 604' can receive full bandwidth signals from the external unit 608. At this point, normal data exchange can occur between the external unit 608 and the implant 604', and then the communication may be terminated.

Figure 13:
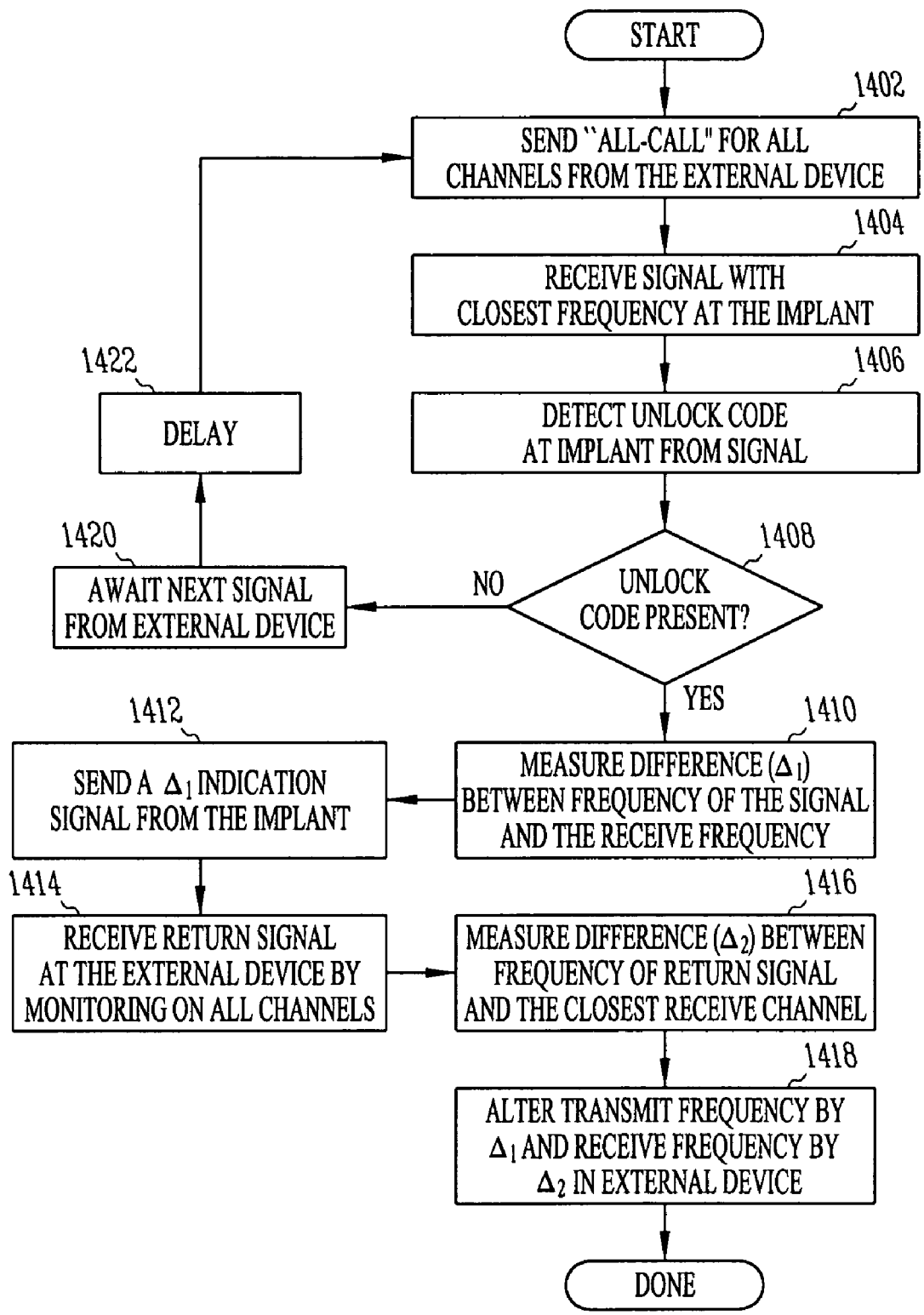
FIG. 13 illustrates another exemplary operational flow of a communication protocol between the external unit and the implantable medical device of FIG. 11 according to one embodiment of the present invention.

An alternative communication protocol for addressing the separate uncertainties of the transmit and receive channels of the implant 604' is illustrated by the operational flow of FIG. 13. Similar to the process of FIG. 12, this process begins by the external unit 608 sending an all-call at send operation 1402. The implant 604' receives a signal of the al-call that has the center frequency closest to the center frequency of the receive channel at receiver operation 1404. The implant looks for the proper unlock code at detect operation 1406, and then query operation 1408 detects whether the proper unlock code was found.

If the unlock code was not found, then the implant 604' awaits the next signal transmission from the external unit 608 at wait operation 1420, and after the delay 1422 the operational flow return is to send operation 1402. If the unlock code is found, then the implant 604' measures the difference $\Delta_1$ between the center frequency of the signal and the center frequency of its receive channel at measure operation 1410. Then, the implant 604' sends an indication return signal at send operation 1412. The indication return signal includes a data packet providing an indication of $\Delta_1$. The indication return signal may be provided with a narrow bandwidth so that the indication return signal may be received by the external unit 608 even though the external unit 608 has not yet accounted for the frequency uncertainties of the implant 604'.

The external unit 608 receives the indication return signal at receive operation 1414 by monitoring on all receive channels. The narrow bandwidth of the indication return signal allows the signal to fall within the bandwidth of a receive channel even though the center frequencies are unaligned. After receiving the indication return signal containing $\Delta_1$, the external unit 608 measures the difference $\Delta_2$ between the center frequency of the indication return signal and the center frequency of the closest receive channel at measure operation 1416. Once $\Delta_2$ is known, the transmit frequency of the external unit 608 is altered by $\Delta_1$ and the receive frequency of the external unit 608 is altered by $\Delta_2$ at alter operation 1418. At this point, the center frequencies for both directions of communication are in alignment and full-bandwidth bidirectional communication proceeds between the external unit 608 and the implant 604'.

The timing of the external unit's attempt to contact the implant 604 and/or the timing of the reverse situation where the implant 604 attempts to contact the external unit 608, must be properly synchronized so that both devices are ready to communicate at the same point in time. The devices 604, 608 are not maintained in a communication-ready state at all times because doing so would deplete the internal power sources too quickly. Therefore, the devices 604, 608 rely upon their internal clocks 710, 810, and/or 1210 to determine when the time for communicating has arrived.

Typically, the processors 706, 804, and/or 1204 are comparing the time from the clocks 710, 810, and/or 1210 to a time schedule to detect the appropriate time to communicate.

Figure 14:
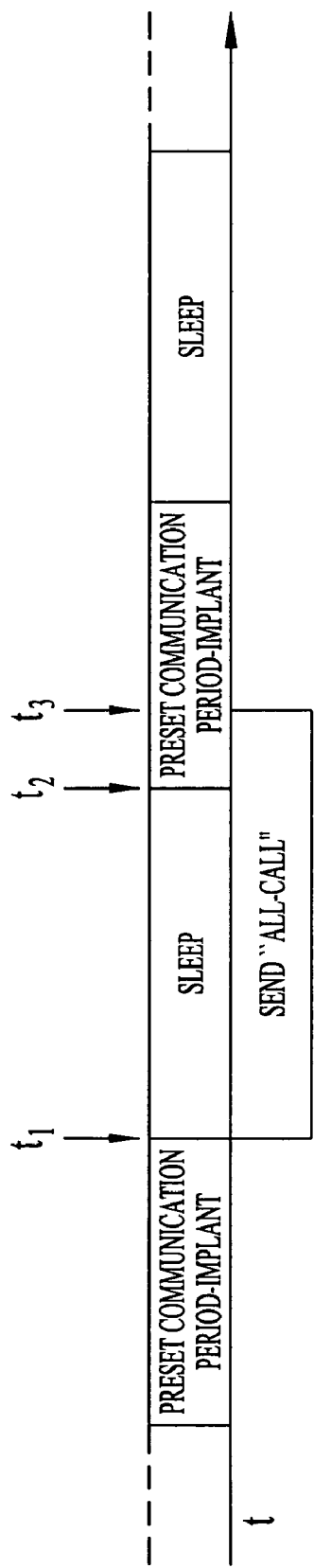
FIG. 14 illustrates a timing of communication between the external unit and the implantable medical device according to one embodiment of the present invention.

An example of a time schedule being followed by processor 706, 804, and/or 1204 is shown in FIG. 14. The implant 604 may have a periodic preset communication periods separated by periodic sleep periods where the communication components such as transmitter/receiver 806, 1206 and/or discriminator 1212 are powered down. Additionally, it may be desirable to power down the communication components of the external unit 608 such as the transmitter/receiver 702 and discriminator 704, especially where the external unit 608 is battery powered. The problem that arises is that the internal clocks 710, 810, and/or 1210 have time drift that occurs so that they are not precisely synchronized for the entire lengths of the sleep periods, and one device may expect communications to occur before the other.

In the example shown in FIG. 14, if the sleep periods, such as from $t_1$ to $t_2$ are relatively short, then one solution to the timing drift problem is to have the external unit 608 periodically attempt to communicate for a length of time greater than the sleep period $t_1$ to $t_2$. The worst case is shown in FIG. 14 where the external unit begins its attempt to communicate with an all-call at the moment in time when the preset communication period for the implant 604 has expired at $t_1$. However, extending the all-call period until $t_3$, which is longer than the sleep period, allows the implant 604 to reach its next preset communication period occurring at $t_2$ and receive the all-call after $t_2$ but before $t_3$.

This approach allows communication to be established during a preset communication period, but there is a tradeoff between the length of the sleep period for the implant 604 and the all-call period for the external unit 608. As the sleep period is increased to save battery life for the implant 604, the all-call period must also be increased to account for improper synchronization and this increase requires more energy per day from the power source of the external unit 608. To avoid this tradeoff, the implant 604 and external unit 608 may be adapted to account for the time drift between the internal clocks 710, 810, and/or 1210.

Figure 15:
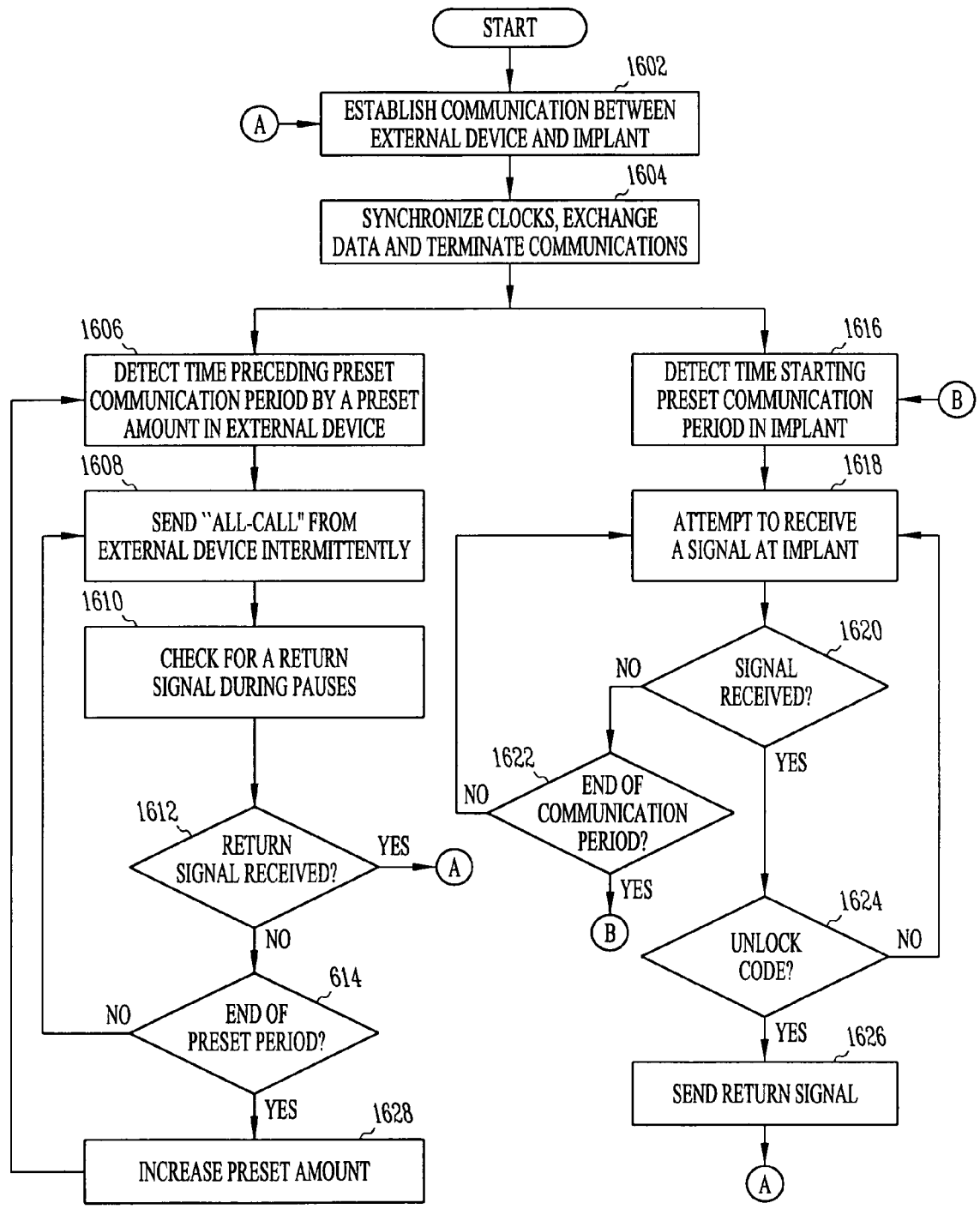
FIG. 15 illustrates an exemplary operational flow of a timing protocol for communications between the external unit and the implantable medical device.

The logical operations for accounting for the time drift are shown in FIG. 15. Initially, communication is established between the external unit 608 and the implant 604 at communication operation 1602, which may account for frequency uncertainties by using the logical operations of FIG. 8, FIG. 12, or FIG. 13. After communication has been established, the clocks 710, 810, and/or 1210 are synchronized to cancel any time drift that has occurred at exchange operation 1604. For example, the external unit 608 may periodically synchronize itself through its external communications to the host system and then can be used as the reference to correct the time of the implant 604. Additionally, at exchange operation the normal data exchange between the implant 604 and external unit 608 occurs and communication is terminated.

At this point, the implant 604 and the external unit 608 begin the sleep periods for the communication components. The operations of the external unit 608 proceed during the sleep period at detect operation 1606 by monitoring for a time that precedes the preset communication period of the implant 604 by a preset amount, but as measured by the internal clock 710 of the external unit 608. When the time preceding the preset communication period occurs, the external unit 608 begins intermittently sending an all-call signal at send operation 1608. During the pauses between the all-call signals, the external unit 608 attempts to receive a return signal from the implant 604 at receive operation 1610.

Query operation 1612 detects whether the return signal has been received. If so, then operational flow returns to communications operation 1602 wherein the communications are established between the external unit 608 and the implant 604. If the query operation 1612 finds that the return signal has not been received, then query operation 1614 detects whether the end of a preset period of the external unit for establishing communications has expired. Typically, the preset period for establishing communications is longer than the preset communication period of the implant 604 by 2 or more times the preset amount used above at detect operation 1606, and therefore should extend beyond the preset communication period of the implant 604 as detected by the implant's clock 810 or 1210.

If query operation 1 614 finds that the end of the preset period of the external unit 608 has not yet expired, then operational flow returns to send operation 1608 where the all-call signals continue to be broadcast. If query operation 1614 finds that the preset communication period has expired, then the opportunity to communicate with the implant 604 on this instance is assumed to be missed and operational flow moves to preset operation 1628, where the preset amount is increased to effectively broaden the broadcast time for the next opportunity to communicate to account for the time drift that has occurred thus far and the additional time drift that will develop until the time for the next opportunity. Operational flow then returns to detect operation 1606 to await the next opportunity as dictated by the time kept by the internal clock 710.

While the external unit 608 performs the functions discussed above during the sleep period, the implant 604 is also active during this time. The sleep period operations of the implant begin at detect operation 1616 where the implant 604 monitors its internal clock 810 or 1210 to detect the start of the preset communication period. Once the beginning of the preset communication period has been found, the implant 604 attempts to receive a signal from the all-call signal at receive operation 1618. Query operation 1620 detects whether the signal has been received.

If no signal has been received, then query operation 1622 detects whether the end of the preset communication period according to the implant's clock 810 or 1210 has expired. If not, then operational flow transitions to receive operation 1618 where the implant 604 continues to look for the signal from the external unit 608. If the end of the preset communication period has arrived, then it is assumed that the opportunity to communicate with the external unit 608 on this instance has been missed. Operational flow then returns to detect operation 1616 to await the next opportunity as dictated by the time kept by the internal clock 810 or 1210.

If query operation 1620 detects that a signal has been received, then query operation 1624 detects whether the signal contains the proper unlock code. If not, then operational flow returns to receive operation 1618 where the implant 604 continues to look for a signal from the external unit 608. If query operation 1624 finds that the signal does contain the proper unlock code, then the implant 604 sends a return signal to the external unit 608 at send operation 1626. Operational flow then returns to communication operation 1602.

Figure 16:
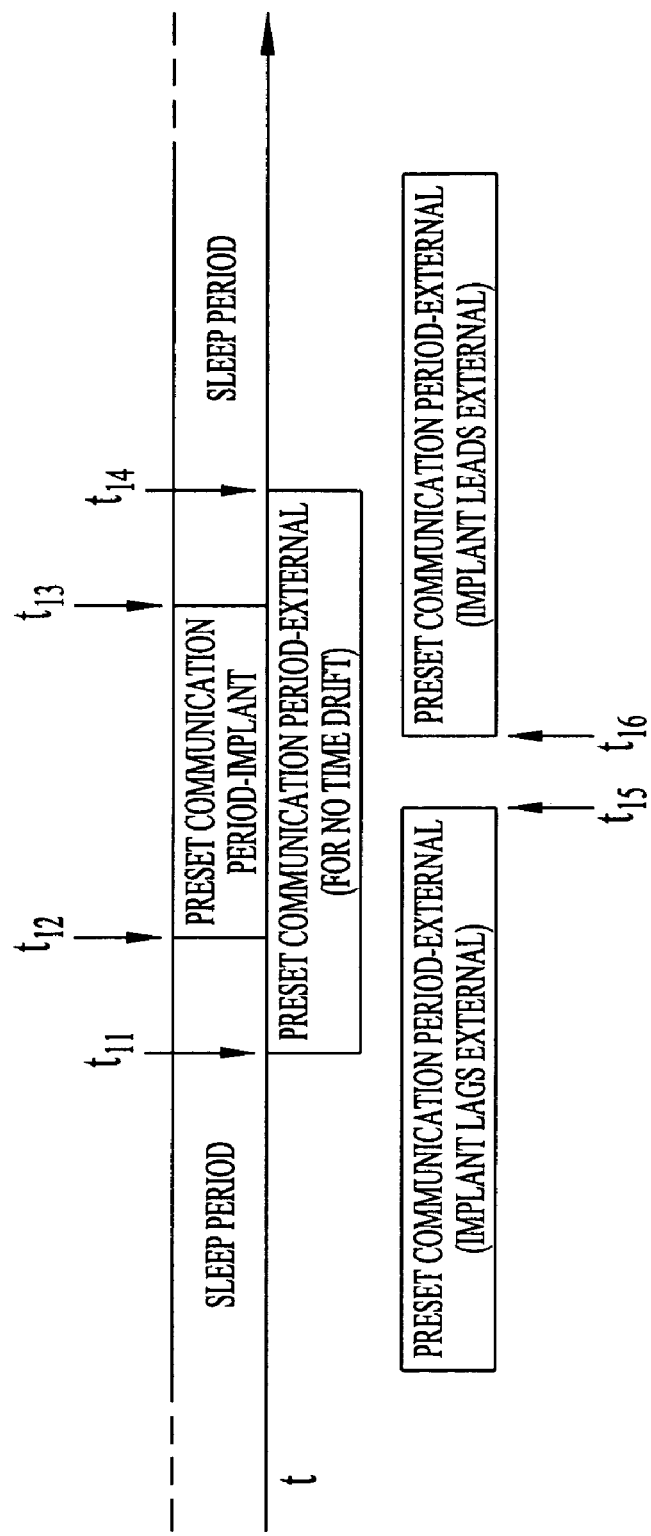
FIG. 16 illustrates a timing of communication between the external unit and the implantable device established by the timing protocol of FIG. 15 in accordance with an embodiment of the present invention.

The time schedule demonstrating three possible scenarios under this scheme of FIG. 15 is shown in FIG. 16. In one scenario, no time drift has occurred and the clocks of the external unit 608 and implant 604 have remained synchronized. The external unit 608 detects that $t_{11}$, the time for the all-call, has arrived. As discussed, this time occurs prior to the time $t_{12}$ when the implant's preset communication period should be starting by some preset amount as detected by the clock 710 of the external unit 608. In this scenario where no time drift has occurred, the preset amount would be the interval from $t_{11}$ to $t_{12}$. The external unit continues to look for the return signal until a return signal is received or until $t_{14}$, which occurs well after the end time $t_{13}$ of the implant's preset communication period.

A scenario where time as kept by the implant 604 lags time as kept by the external unit 608 is also shown The preset communication period occurring for the external unit 608 begins well before $t_{11}$ (the no drift case) and before $t_{12}$, which is the start of the preset communication period as measured by the clock 810 or 1210 of the implant 604. This preset communication period of the external unit 608 extends until $t_{15}$, which occurs after time $t_{12}$ that is the time when the implant 604 begins attempting to receive the signal. Because there is some overlap between the communication period of the implant 604 and the communication period of the external unit 608, communication can be established.

The opposite scenario is also shown, wherein time as kept by the implant 604 leads time as kept by the external unit 608. The preset communication period occurring for the external unit 608 begins after $t_{11}$ (the no drift case) and after $t_{12}$, which is the start of the preset communication period as measured by the clock 810 or 1210 of the implant 604. However, the preset communication period of the external unit 608 begins before the time $t_{13}$ that is the time when the implant 604 stops attempting to receive the signal. Again, because there is some overlap between the communication period of the implant 604 and the communication period of the external unit 608, communication can be established.

Each time communication is established, the clocks 710, 810, and/or 1210 of the implant 604 and the external unit 608 are synchronized at exchange operation 1604. Therefore, the offset in time between the two clocks does not continue to build. For situations where an opportunity to communicate has been missed because the time drift was larger than expected, the increase in the preset amount of time utilized by the external unit 608 at preset operation 1628 accounts for the time drift build, and overlap of the communication periods may occur at the next opportunity.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. A method of establishing communication between an implantable medical device and an external unit wherein the implantable medical device has a transmit and a receive frequency that are separated by a fixed difference, comprising the steps of:

sending out one or more signals from the external unit, wherein one signal of the one or more signals has a frequency that is close enough to the receive frequency for the implantable device to receive the one signal;

receiving the one signal at the implantable medical device;

sending out a return signal at a transmit frequency from the implantable medical device in response to receiving the one signal;

receiving the return signal at the external unit;

measuring a difference between the transmit frequency of the return signal and a receive frequency of the external unit; and altering a transmit frequency and the receive frequency of the external unit by the measured difference.

2. The method of claim 1, wherein the step of sending out one or more signals comprises simultaneously sending a plurality of signals that have frequencies that fall in a frequency range where the receive frequency lies, and wherein the step of receiving the one signal comprises receiving the one signal of the plurality of signals that has the frequency that is closest to the receive frequency.

3. The method of claim 2, wherein the step of measuring a difference comprises measuring a difference between the transmit frequency of the return signal and a receive frequency of a plurality of receive frequencies of the external unit that is closest to the transmit frequency.

4. The method of claim 2, wherein the step of receiving the return signal comprises simultaneously receiving all of a set of receive frequencies of the external unit.

5. The method of claim 2, wherein the step of receiving the return signal comprises sequentially receiving each frequency of a set of receive frequencies of the external unit.

6. The method of claim 1, further comprising:

delaying sending out the one or more signals for a preset amount of delay time after sending out the one or more signals for a preset amount of send time;

attempting to receive the return signal at the external unit during the delay time; and repeating the steps of sending the one or more signals and delaying sending out the one or more signals when no return signal is received during the delay time.

7. The method of claim 6, wherein the step of sending out the one or more signals for the preset amount of send time involves sending out the one or more signals for a send time that is greater than a duration of preset communication periods of the implantable medical device, and wherein the step of sending out the one or more signals at least partially overlaps in time with an occurrence of the preset communication period.

8. The method of claim 6, wherein the step of sending out the one or more signals for the preset amount of send time involves sending out the one or more signals for a send time that is greater than a period between preset communication periods of the implantable medical device, and wherein the step of sending out the one or more signals at least partially overlaps in time with an occurrence of the preset communication period.

9. The method of claim 1, further comprising:

encoding an unlock code in the one or more signals prior to the step of sending out the one or more signals; and prior the step of sending the return signal, decoding the unlock code from the one signal received by the implantable medical device.

10. The method of claim 1, wherein the step of sending one or more signals comprises sending one or more signals that each occupy bandwidth that is less than a bandwidth used to communicate with the implantable device after the transmit and receive frequencies have been altered.

11. A method of establishing communication between an implantable medical device and an external unit wherein the implantable medical device has a transmit frequency and a receive frequency, comprising the steps of:

sending one or more signals from the external unit wherein one signal of the one or more signals has a frequency that is close enough to the receive frequency for the implantable device to receive the one signal;

receiving the one signal at the implantable medical device;

measuring a first difference between the frequency of the one signal and the receive frequency;

sending out one or more return signals at the transmit frequency from the implantable medical device, wherein one of the one or more return signals includes an indication of the first difference;

receiving the one or more return signals at the external unit;

detecting the first difference from the indication included in one of the one or more return signals at the external unit;

measuring a second difference between the transmit frequency of the one or more return signals and a receive frequency of the external unit;

altering the transmit frequency of the external unit by the first difference; and altering the receive frequency of the external unit by the second difference.

12. The method of claim 11, wherein the step of sending out one or more signals comprises simultaneously sending a plurality of signals that have frequencies that fall in the frequency range where the receive frequency lies, and wherein the step of receiving the one signal comprises receiving the one signal of the plurality of signals that has the frequency that is closest to the receive frequency.

13. The method of claim 12, wherein the step of measuring the second difference comprises measuring the second difference between the transmit frequency of the return signal and a receive frequency of a plurality of receive frequencies of the external unit that is closest to the transmit frequency.

14. The method of claim 12, wherein the step of receiving the one or more return signals comprises simultaneously receiving all of a set of receive frequencies of the external unit.

15. The method of claim 12, wherein the step of receiving the one or more return signals comprises sequentially receiving each frequency of a set of receive frequencies of the external unit.

16. The method of claim 11, further comprising:

delaying sending out the one or more signals for a preset amount of delay time after sending out the one or more signals for a preset amount of send time;

attempting to receive the one or more return signals at the external unit during the delay time; and repeating the steps of sending the one or more signals and delaying sending out the one or more signals when no return signal is received during the delay time.

17. The method of claim 16, wherein the step of sending out the one or more signals for the preset amount of send time involves sending out the one or more signals for a send time that is greater than a duration of preset communication periods of the implantable medical device, and wherein the step of sending out the one or more signals at least partially overlaps in time with an occurrence of the preset communication period.

18. The method of claim 16, wherein the step of sending out the one or more signals for the preset amount of send time involves sending out the one or more signals for a send time that is greater than a period between preset communication periods of the implantable medical device, and wherein the step of sending out the one or more signals at least partially overlaps in time with an occurrence of the preset communication period.

19. The method of claim 11, further comprising:
encoding an unlock code in the one or more signals prior to the step of sending out the one or more signals; and
prior the step of sending the return signal, decoding the unlock code from the one signal received by the implantable medical device.

20. The method of claim 11, wherein the step of sending one or more signals comprises sending one or more signals that each occupy bandwidth that is less than a bandwidth used to communicate with the implantable device after the transmit and receive frequencies have been altered.

21. A method of periodically establishing communication between an implantable medical device and an external unit wherein the implantable medical device has a clock that triggers a preset communication period, comprising the steps of:
establishing an initial communication between the external unit and the implantable medical device;
synchronizing a clock in the external unit with the clock of the implantable medical device during the initial communication;
after the initial communication is terminated, detecting a time with the clock of the external unit that is earlier than the preset communication period as measured by the clock of the external unit by a preset amount; and
sending a signal on one or more frequencies from the external unit beginning at the detected time and extending for an amount of time greater than the preset communication period as measured by the clock of the external unit or until a return signal is received from the implantable device.

22. The method of claim 21, further comprising increasing the preset amount when a return signal is not received during a period of sending the signal of the one or more frequencies.

23. The method of claim 21, wherein the implantable device has transmit and receive frequencies with a fixed difference between them, the method further comprising the steps of:
receiving a return signal from the implantable device in response to sending the signal from the external unit; and
altering transmit and receive frequencies of the external unit based on a difference between a frequency of the return signal and the receive frequency of the external unit.

24. The method of claim 23, further comprising the steps of:
receiving a return signal from the implantable device in response to sending the signal, wherein the return signal includes an indication of a difference between the frequency of the signal received by the implantable device and a receive frequency of the implantable device;
altering a receive frequency of the external unit based on a difference between a frequency of the return signal and the receive frequency of the external unit; and
altering a transmit frequency of the external unit based on the indication included in the return signal.

25. An external unit for communicating with an implantable medical device, the external unit comprising:
a transmitter having an adjustable frequency, wherein the transmitter sends a signal at one or more frequencies to the implantable medical device;
a receiver having an adjustable frequency, wherein the receiver receives a return signal at a return frequency from the implantable device;
a frequency discriminator that detects a difference between a receive frequency of the receiver and the return frequency of the return signal received by the receiver; and
a processor configured to alter a transmit frequency of the transmitter and the receive frequency of the receiver according to the frequency difference.

26. The external unit of claim 25, wherein the difference in frequency between the transmit frequency of the transmitter and the frequency of the receiver is fixed.

27. The external unit of claim 25, wherein the transmitter and receiver have frequency synthesizers.

28. The external unit of claim 25, wherein the processor is further configured to encode an unlock code in the signal that the transmitter sends.

29. An external unit for communicating with an implantable medical device, the external unit comprising:
a transmitter having an adjustable frequency, wherein the transmitter sends a signal on one or more frequencies to the implantable medical device;
a receiver having an adjustable frequency, wherein the receiver receives one or more return signals at a return frequency from the implantable medical device;
a frequency discriminator that detects a difference between the return frequency of the one or more return signals and a receive frequency of the receiver; and
a processor configured to control the frequency of the transmitter and receiver, alter the receiver frequency according to the frequency difference, detect a frequency difference indicator encoded in one of the one or more return signals received by the receiver, and alter a transmit frequency of the transmitter according to the frequency difference indicator.

30. The external unit of claim 29, wherein the transmitter and receiver have frequency synthesizers.

31. The external unit of claim 29, wherein the processor is further configured to encode an unlock code in the signal that the transmitter sends.

32. An implantable medical device for communicating with an external unit, the implantable device comprising:
a transmitter with a transmit frequency, wherein the transmitter sends a return signal to the external unit at the transmit frequency;
a receiver with a receive frequency that differs in frequency from the transmit frequency, wherein the receiver receives a signal at a frequency transmitted by the external unit;
a frequency discriminator that detects a difference between the frequency of the signal received by the receiver and the receive frequency; and
a processor configured to encode an indication of the difference in the return signal transmitted by the transmitter.

33. The medical device of claim 32, further comprising a clock, and wherein the processor is further configured to enable the receiver to receive at pre-set communication period determined from the clock, and wherein the processor is configured to test the signal received by the receiver during the pre-set communication period for an unlock code.

34. An external unit for communicating with an implantable medical device, the external unit comprising:
transmit means for sending a signal at one or more frequencies to the implantable medical device;

receive means for receiving a return signal at a return frequency from the implantable device;

discriminator means for detecting a difference between a receive frequency of the receive means and the return frequency of the return signal received by the receive means; and processing means for altering a transmit frequency of the transmit means and the receive frequency of the receive means according to the frequency difference.

35. The external unit of claim 34, wherein the difference in frequency between the transmit frequency of the transmit means and the frequency of the receive means is fixed.

36. The external unit of claim 34, wherein the transmit means and receive means have frequency synthesizers.

37. The external unit of claim 34, wherein the processing means is for encoding an unlock code in the signal that the transmit means sends.

38. An external unit for communicating with an implantable medical device, the external unit comprising:

a transmit means for sending a signal on one or more frequencies to the implantable medical device;

a receive means for receiving one or more return signals at a return frequency from the implantable medical device;

discriminator means for detecting a difference between the return frequency of the one or more return signals and a receive frequency of the receive means; and processing means for controlling the frequency of the transmit means and receive means, altering the receive means frequency according to the frequency difference, detecting a frequency difference indicator encoded in one of the one or more return signals received by the receive means, and altering a transmit frequency of the transmit means according to the frequency difference indicator.

39. The external unit of claim 38, wherein the transmit means and receive means have frequency synthesizers.

40. The external unit of claim 38, wherein the processing means is for encoding an unlock code in the signal that the transmit means sends.

41. An implantable medical device for communicating with an external unit, the implantable device comprising:

transmit means for sending a return signal at a transmit frequency to the external unit at a return frequency;

receive means for receiving a signal transmitted by the external unit;

discriminator means for detecting a difference between the frequency of the signal received by the receive means and a receive frequency of the receive means; and processing means for encoding an indication of the difference in the return signal transmitted by the transmit means.

42. The implantable medical device of claim 41, further comprising a clock, and wherein the processing means is for enabling the receive means to receive at pre-set communication periods determined from the clock, and wherein the processing means is for testing the signal received by the receive means during the pre-set communication periods for an unlock code.

43. The implantable medical device of claim 41, wherein the transmit frequency and the receive frequency are not separated by a fixed amount.

\* \* \* \* \*